United States Patent [19]

Vlasuk et al.

[11] Patent Number: 5,886,146

[45] Date of Patent: *Mar. 23, 1999

[54] INHIBITORS OF THROMBOSIS

[75] Inventors: George P. Vlasuk, Carlsbad; Thomas R. Webb, Encinitas; Daniel A. Pearson; Matthew M. Abelman, both of Solana Beach, all of Calif.

[73] Assignee: Corvas International, Inc., San Diego, Calif.

[ * ] Notice: The term of this patent shall not extend beyond the expiration date of Pat. No. 5,492,895.

[21] Appl. No.: 459,705

[22] Filed: Jun. 2, 1995

Related U.S. Application Data

[63] Continuation of Ser. No. 195,995, Feb. 14, 1994, which is a continuation-in-part of Ser. No. 17,125, Feb. 12, 1993, abandoned, and Ser. No. 836,123, Feb. 14, 1992, abandoned.

[51] Int. Cl.$^6$ .................................................... A61K 38/06

[52] U.S. Cl. .................................. 530/331; 514/18; 514/19

[58] Field of Search ......................... 514/18, 19; 530/331

[56] References Cited

U.S. PATENT DOCUMENTS

| 5,492,895 | 2/1996 | Vlasuk | 514/18 |
| 5,534,498 | 7/1996 | Brunck | 514/19 |

FOREIGN PATENT DOCUMENTS 9207869  5/1992  WIPO.

*Primary Examiner*—Cecilia J. Tsang
*Assistant Examiner*—David Lukton
*Attorney, Agent, or Firm*—Lyon & Lyon LLP

[57] ABSTRACT

This invention relates to peptide aldehyde analogs that inhibit the thrombin or Factor Xa. The compounds are thought useful for preventing or treating conditions in mammal characterized by abnormal thrombosis.

12 Claims, 3 Drawing Sheets

INHIBITORS OF THROMBOSIS

RELATED APPLICATIONS

This is a continuation of application Ser. No. 08/195,995, filed Feb. 14, 1994, which is a continuation-in-part of U.S. Ser. No. 08/017,125, filed Feb. 12, 1993 and U.S. Ser. No. 07/836,123, filed Feb. 14, 1992, now abandoned, which are hereby incorporated by reference herein, including the drawings attached thereto.

FIELD OF INVENTION

In one aspect, the present invention relates compounds which are potent inhibitors of thrombin or factor Xa. In another aspect, the present invention relates to novel peptide aldehyde analogs, their pharmaceutically acceptable salts, and pharmaceutically acceptable compositions thereof which are useful as potent and specific inhibitors of blood coagulation in mammals. In yet another aspect, the invention relates to methods of using these inhibitors as therapeutic agents for disease states in mammals characterized by abnormal thrombosis.

BACKGROUND OF INVENTION

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation. These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways. The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

Proteolytic activation of zymogen factor X to its catalytically active form, factor Xa, results in the liberation of a 52 amino acid activation peptide from the amino-terminus of the heavy chain subunit. The intrinsic activation reaction is catalyzed by factor IXa in a macromolecular complex with the non-enzymatic co-factor, factor VIIIa. Factor Xa formation via the extrinsic pathway is catalyzed by the catalytic complex of factor VIIa and tissue factor. Both of these reactions must occur on an appropriate phospholipid surface in the presence of calcium ions. The active product formed following either intrinsic or extrinsic activation of factor X is α-factor Xa. A second proteolytic cleavage which is thought to be autocatalytic, results in the formation of β-factor Xa following the release of a 14 amino acid peptide from the carboxy-terminus of the heavy chain. Both forms of the activated molecule have the same catalytic activity as measured by their ability to promote coagulation in plasma or hydrolyze a peptidyl chromogenic substrate.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 5: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet α-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. There is currently no effective therapy for the treatment or prevention of acute arterial thrombosis or rethrombosis since heparin, the most widely used clinical anticoagulant administered i.v., has not been shown to be universally effective in this setting. Prins, M. H. and Hirsh, J., J. Am. Coll. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of factor Xa as the catalyst for the penultimate step in the blood coagulation cascade which is the formation of the serine protease thrombin.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

```
P4     P3     P2     P1  P1'
Gly — Gly — Val — Arg/Gly   Fibrinogen Aα Chain Phe — Ser — Ala — Arg/Gly   Fibrinogen Bβ Chain
```

Peptidyl derivatives having an uncharged residue in the P3 position which is believed to bind to the active site of thrombin and thereby inhibit the conversion of fibrinogen to fibrin and cellular activation have been reported. Additionally, these derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which are said to differ in structure to those containing a uncharged amino acid in the P3 recognition subsite have been reported. The compound, Argatroban (also called 2R,4R-4-methyl-1-[N-2-(3-methyl-1,2,3,4-tetrahydro-8-quinolinesulfonyl)-L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to the active site and another site on the enzyme have been reported. Hirudin and its various peptidyl derivatives have been reported to inhibit both conversion of fibrinogen to fibrin and platelet activation by binding to either the active site and exo site, or exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It is reported to inhibit thrombin by binding to both its anion-binding exo-site and to its catalytic active site which are distinct and physically distant from each other. Rydel, supra. Hirudin has been reported to be a potent antithrombotic agent in vivo. Markwardt, F. et al., Pharmazie, 43: 202 (1988); Kelly, A. B. et al., Blood, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 265: 13484 (1990). The region of hirudin represented by hirugen has been reported, as according to by x-ray crystallographic analysis, to bind directly to the exo site of thrombin. Skrzypczak-Jankun, E. et al., Thromb. Haemostas., 6: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, supra. Hirugen also is reported to block thrombin-mediated platelet aggregation. Jakubowski, J. A. and Maraganore, J. M., Blood, 75: 399 (1990).

Hirulog has been reported to be a synthetic chimeric molecule comprised of a hirugen-like sequence linked by a glycine-spacer region to the peptide, D-phenylalanyl-prolyl-arginine which is based on a preferred substrate recognition site for thrombin. The hirugen-like sequence is said to be linked to this peptide through the C-terminal end of the peptide. Maraganone, J. M. et al., Biochemistry, 29: 7095 (1990). Hirulog has been reported to be an effective anti-thrombotic agent in preventing both fibrin-rich and platelet-rich thrombosis. Maraganone, J. M. et al., Thromb. Haemostas., 6: 651 at abstract 17 (1991).

SUMMARY OF THE INVENTION

In one aspect, the present invention is directed to compounds which are useful as antithrombic agents.

In one aspect, the present invention provides compounds of the formula:

AcR-A$_1$-L-Pro-L-Arg-al (II)

wherein ACR is a hydrophobic acyl or hydrophobic sulfonyl group, and A$_1$ is glutamic acid (Glu) or aspartic acid (Asp), or an equivalent of Glu or Asp, which has an IC$_{50}$ for thrombin and/or Factor Xa of about 200 nM or less and an IC$_{50}$ for plasmin which is greater than the smaller of the IC$_{50}$ for thrombin or for Factor Xa. These compounds are useful as inhibitors of thrombosis.

According to a preferred aspect, compounds of the present invention include those of formula:

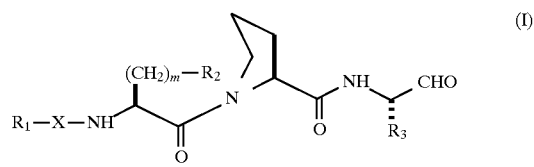

wherein (a) R$_1$ is selected from the group consisting of alkyl of about 5 to about 10 carbon atoms if X is —C(=O)— or —O—C(=O)— or alkyl of 1 to about 10 carbon atoms if X is —S(O$_2$)—, —NH—S(O$_2$)— or —O—S (O$_2$)—; alkyl of 1 to about 3 carbon atoms substituted with cyclic alkyl of about 5 to about 8 carbon atoms; alkenyl of about 3 to about 6 carbon atoms optionally substituted with cyclic alkyl of about 5 to about 8 carbon atoms; aryl of about 6 to about 14 carbon atoms which is optionally mono-substituted with Y$_1$ or optionally di-substituted with Y$_1$ and Y$_2$; aralkyl of about 6 to about 15 carbon atoms which is optionally mono-substituted in the aryl ring with Y$_1$ or optionally di-substituted in the aryl ring with Y$_1$ and Y$_2$; aralkenyl of about 8 to about 15 carbon atoms which is optionally mono-substituted in the aryl ring with Y$_1$ or optionally di-substituted in the aryl ring with Y$_1$ and Y$_2$; perfluoroalkyl of 1 to about 12 carbon atoms; perfluoroaryl of about 6 to about 14 carbon atoms; trimethylsilylalkyl of 4 to about 8 carbon atoms;

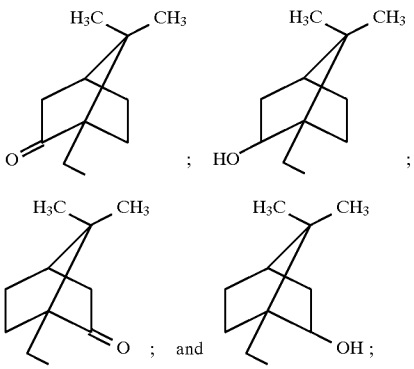

wherein $Y_1$ and $Y_2$ are independently selected from the group consisting of bromo, chloro, fluoro, $Z_1$—, HO—, $Z_1$—O—, $NH_2$—, $Z_1$—NH—, $(Z_1,Z_2)$N—, $Z_1$—C(O)—NH—, HS—, $Z_1$—S—, $Z_1$—S(O)—, $Z_1$—S($O_2$)—, HO—S($O_2$)—, $Z_1$—O—S($O_2$)—, $NH_2$—S($O_2$)— and $Z_1$—NH—S($O_2$)—, wherein $Z_1$ and $Z_2$ are independently selected from the group consisting of trifluomethyl, pentafluoroethyl, alkyl of 1 to about 12 carbon atoms, aryl of about 6 to about 14 carbon atoms, and aralkyl of about 6 to about 15 carbon atoms;

(b) X is —C(=O)—, —O—C(=O)—, —S($O_2$)—, —NH—S($O_2$)—, —O—S($O_2$)—;

(c) m is 1 or 2;

(d) $R_2$ is —$CO_2$H, —$CO_2$R', or

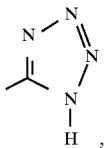

wherein R' is alkyl of 1 to about 4 carbon atoms, aryl of about 6 to about 14 carbon atoms, or arakyl of about 6 to about 14 carbon atoms; and (e) $R_3$ is —$(CH_2)_3$—NH—C(=NH)—$NH_2$; or a pharmaceutically acceptable salts thereof.

Peptidyl arginine aldehydes have been reported to exist in equilibrium structures in aqueous solutions. Bajusz, S., et al., J. Med. Chem., 33: 1729 (1990). These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all its equilibrium forms.

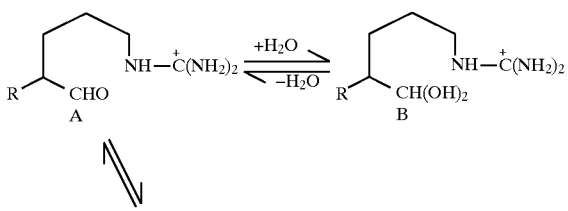

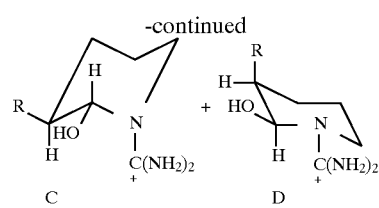

In another aspect, the present invention includes pharmaceutical compositions comprising a therapeutically effective amount of the compounds above and a pharmaceutically acceptable carrier. In yet another aspect, the present invention includes methods of using the above compounds and pharmaceutical compositions for preventing or treating disease states characterized by disorders of the blood coagulation process in mammals.

Definitions

In accordance with the present invention and as used herein, the following terms are defined with the following meanings, unless explicitly stated otherwise.

The term "alkyl" refers to saturated aliphatic groups including straight-chain, branched-chain and cyclic groups.

The term "alkenyl" refers to unsaturated hydrocarbyl groups which contain at least one carbon-carbon double bond and includes straight-chain, branched-chain and cyclic groups.

The term "aryl" refers to aromatic groups which have at least one ring having a conjugated pi electron system and includes carbocyclic aryl, heterocyclic aryl and biaryl groups, all of which may be optionally substituted.

The term "aralkyl" refers to an alkyl group substituted with an aryl group. Suitable aralkyl groups include benzyl, picolyl, and the like, all of which may be optionally substituted.

The term "aralkenyl refers to an alkenyl group substituted with an aryl group. Suitable aralkenyl groups include styrenyl and the like, all of which may be optionally substituted.

The term "alkylene" refers to a divalent straight chain or branched chain saturated aliphatic radical.

The term "alkylenecarboxy" refers to the group -alkCOOH where alk is alklene.

The term "carboxamide" refers to the group —C(O)—$NH_2$.

The term "alkylenecarboxamide" refers to the group -alk-C(O)$NH_2$ where alk is alkylene.

The term "alkylenehydroxy" refers to the group -alk-OH wherein alk is alkylene.

The term "amino acid" refers to both natural and unnatural amino acids in either their L- or D- forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Mety), phenylalanine (Phe), proline (Pro), serine (Ser), threonine (Thr), tryptophan (Trp), tyrosine (Tyr) and valine (Val). For example, unnatural amino acids include, but are not limited to azetidinecarboxylic acid, 2-aminoadipic acid, 3-aminoadipic acid, β-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid.

The term "amino acid residue" refers to —NH—CH(R)—CO—, wherein R is the side chain group distinguishing each amino acid. For cyclic amino acids, the residue is

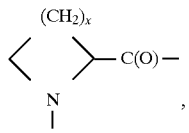

wherein x is 1, 2 or 3 representing the azetidinecarboxylic acid, proline or pipecolic acid residues, respectively.

The term "hydrophobic acyl group" refers to a $R_1$—C(=O)— group, wherein $R_1$ is an alkyl, aryl, aralkyl or other non-polar grouping.

The term "hydrophobic sulfonyl group" refers to a $R_1$—S($O_2$)— group, wherein $R_1$ is an alkyl, aryl, aralkyl or other non-polar grouping.

The term "methylene" refers to —$CH_2$—.

The term "perfluoroalkyl refers to an alkyl group wherein each hydrogen is replaced by a fluoro. Suitable perfluoroalkyl groups include perfluoromethyl (having the structure of $CF_3$—) and perfluroethyl (having the structure of $CF_3$—$CF_2$—) and the like.

The term "perfluoroaryl refers to an aryl group wherein each hydrogen is replaced by a fluoro. Suitable perfluoroaryl groups include perfluorophenyl (having the formula of

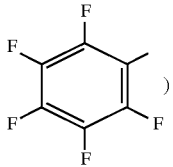

and 2-perfluoronaphthyl (having the formula of

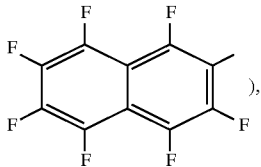

and the like.

In addition, the following abbreviations stand for the following:

"Ala(Tzl)" refers to (R)-3-tetrazolyl-2-aminopropionic acid.
"Arg-al" refers to L-argininal.
"Asp" refers to L-aspartic acid.
"Asp(OCH$_3$)" refers to L-aspartic acid β-methyl ester.
"Bn" refers to benzyl.
"BzlSO$_2$" refers to benzylsulfonyl.
"Boc" refers to t-butoxycarbonyl.
"BocPro-OH" refers to N-Boc-L-proline.
"Bom" refers to benzyloxymethyl.
"BOP" refers to benzotriazol-1-yloxy-tris-(dimethylamino)-phosphonium-hexafluorophosphate.
"Brine" means an aqueous saturated solution of sodium chloride.
"n-BuSO$_2$" refers to n-butylsulfonyl.
"Cbz" refers to benzyloxycarbonyl.
"CDI" refers to carbonyldiimidazole.
"ChxAc" refers to 1-cyclohexylacetyl.
"ChxPA" refers to 3-cyclohexylpropanoyl.
"DCM" refers to dichloromethane.
"DIEA" refers to diisopropylethylamine.
"DMF" refers to N,N-dimethylformamide.
"EtOAc" refers to ethyl acetate.
"EDC" refers to ethyl-3-(3-dimethylamino)propylcarbodiimide hydrochloride salt.
"Fm" refers to 9-fluorenemethyl.
"HOBt" refers to 1-hydroxybenzotriazole monohydrate.
"HCA" refers to 3-phenylpropionyl.
"IPA" refers to isopropanol.
"αMeHCA" refers to 2-methyl-3-phenylpropionyl.
"MeOH" refers to methanol.
"4-MePhSO$_2$" refers to 4-methylphenylsulfonyl
"4MeV" refers to 4-methylpentanoyl.
"NaOAc" refers to sodium acetate.
"NpAc" refers to 1-naphthylacetyl.
"2-NpSO$_2$" refers to 2-naphthylsulfonyl.
"NMM" refers to 4-methylmorpholine.
"Oct" refers to octanoyl.
"Ph" refers to phenyl group.
"Pro" refers to L-proline.
"2PrPent" refers to 2-propylpentoyl.
"TBTU" refers to 2-(1H-benzotriazol-1-yl)-1,1,3,3-tetramethyluronium tetrafluoroborate.
"TEA" refers to triethylamine.
"TFA" refers to trifluoroacetic acid.
"THF" refers to tetrahydrofuran.

DETAILED DESCRIPTION OF THE PREFERRED EMBODIMENTS PREFERRED COMPOUNDS

Figure 1:
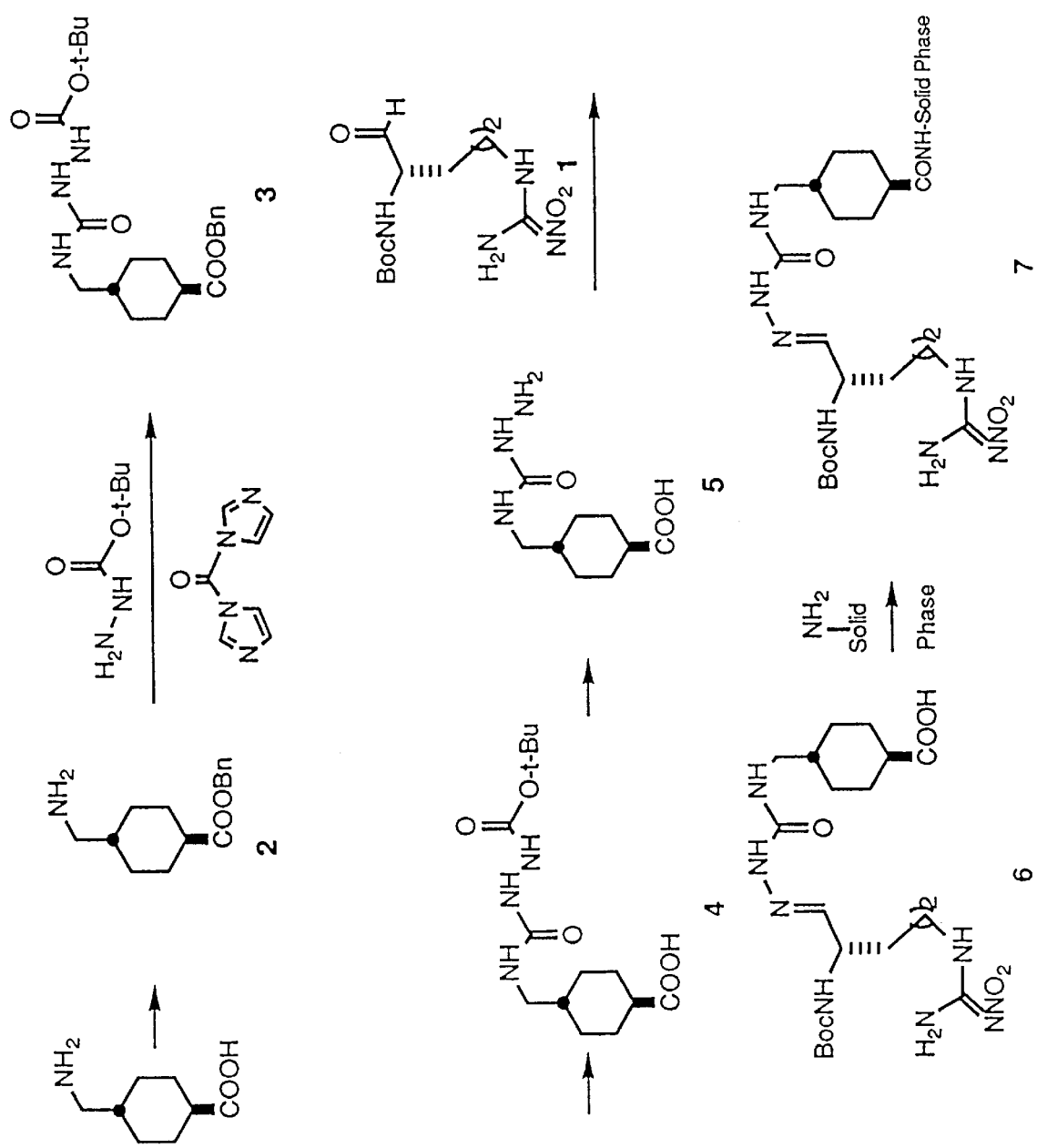
FIG. 1 depicts a reaction scheme describing a process for preparing a solid-phase reagent which is subsequently used to make one or more of the compounds of the present invention. In this figure, Bn refers to benzyl; t-Bu refers to t-butyl; and Boc refers to t-butoxycarbonyl.

According to a preferred aspect, the present invention is directed to compounds of the formula:

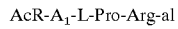

(II)

wherein AcR is a hydrophobic acyl or hydrophobic sulfonyl group, and $A_1$ is glutamic acid (Glu) or aspartic acid (Asp), or an equivalent of Glu or Asp, which has an $IC_{50}$ for thrombin and/or Factor Xa of about 200 nM or less and an $IC_{50}$ for plasmin which is greater than the smaller of the $IC_{50}$ for thrombin or for Factor Xa.

By "equivalent" is meant to include variations in the general structure of amino acid, $A_1$, or the hydrophobic acyl or hydrophobic sulfonyl group which have little if any deleterious effect on the inhibitory activity of the compound compared to the use of the designated amino acid or hydrophobic acyl or hydrophobic sulfonyl group. In general, suitable hydrophobic acyl groups will have at least about 5 carbon atoms in addition to the acyl (carbonyl) carbon and will be hydrophobic enough to provide a potent inhibitory activity. Likewise, suitable hydrophobic sulfonyl groups will have at least about 5 carbon atoms in addition to the sulfonyl sulfur and will be hydrophobic enough to provide a potent inhibitory activity. The Glu or Asp is a carboxylated non-cyclic amino acid and equivalents thereof. Such equivalents would include γ-R' esters of glutamic acid, β-R' esters of aspartic acid, or R'-substituted tetrazoles where the tetrazole substituted for the carboxylic acid group of Glu or Asp. R' in these equivalents is H, lower alkyl of 1 to 6 carbons, aryl of 6 to 14 carbons, or aralkyl of about 6 to about 15 carbon atoms.

One aspect of the present invention is directed to derivatives of certain peptide aldehydes. These compounds are depicted in formula (IA) below:

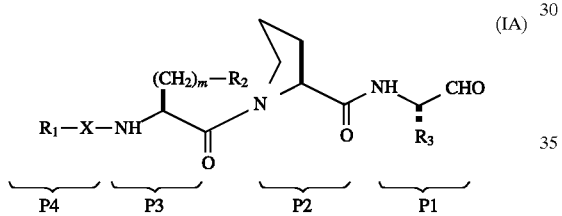

(IA)

Preferred compounds of formula (IA) include those where the $R_3$ group is —$(CH_2)_3$—NH—C(=NH)—$NH_2$. That is, where P1 is L-argininal.

Preferred compounds also include those in which the P2 residue is L-proline.

Preferred compounds further include those in which m is 1 or 2.

Preferred compounds further include those in which $R_2$ is —$CO_2H$, —$CO_2R'$,

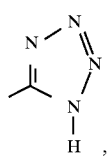

wherein R' is alkyl of 1 to about 4 carbon atoms, aryl of about 6 to about 14 carbon atoms, or arakyl of about 6 to about 14 carbon atoms. Especially preferred compounds are those wherein R' is methyl.

Preferred compounds further include those in which P4 (i.e., R1—X—) is a blocking group, that is, a group which is blocks the terminal amino group of the P3 group. These include those blocking groups wherein:

(1) X is —C(=O)—, —O—C(=O)—, —$S(O_2)$—, —NH—$S(O_2)$—, or —O—$S(O_2)$— and (2) $R_1$ is selected from the group consisting of alkyl of about 5 to about 10 carbon atoms if x is —C(=O)— or —O—C(=O)— or alkyl of 1 to about 10 carbon atoms if X is —$S(O_2)$—, —NH—$S(O_2)$— or —O—$S(O_2)$—; alkyl of 1 to about 3 carbon atoms substituted with cyclic alkyl of about 5 to about 8 carbon atoms; alkenyl of about 3 to about 6 carbon atoms optionally substituted with cyclic alkyl of about 5 to about 8 carbon atoms; aryl of about 6 to about 14 carbon atoms which is optionally mono-substituted with $Y_1$ or optionally di-substituted with $Y_1$ and $Y_2$; aralkyl of about 6 to about 15 carbon atoms which is optionally mono-substituted in the aryl ring with $Y_1$ or optionally di-substituted in the aryl ring with $Y_1$ and $Y_2$; aralkenyl of about 8 to about 15 carbon atoms which is optionally mono-substituted in the aryl ring with $Y_1$ or optionally di-substituted in the aryl ring with $Y_1$ and $Y_2$; perfluoroalkyl of 1 to about 12 carbon atoms; perfluoroaryl of about 6 to about 14 carbon atoms;, trimethylsilylalkyl of 4 to about 8 carbon atoms;

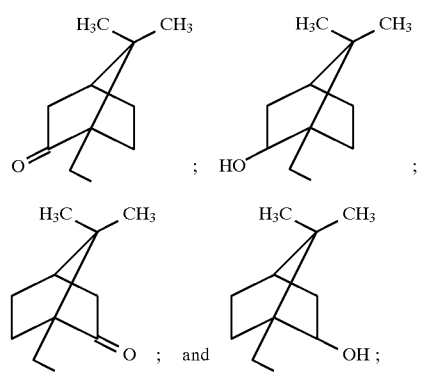

wherein $Y_1$ and $Y_2$ are independently selected from the group consisting of bromo, chloro, fluoro, $Z_1$—, HO—, $Z_1$—O—, $NH_2$—, $Z_1$—NH—, $(Z_1,Z_2)$N—, $Z_1$—C(O)—NH—, HS—, $Z_1$—S—, $Z_1$—S(O)—, $Z_1$—$S(O_2)$—, HO—S$(O_2)$—, $Z_1$—O—$S(O_2)$—, $NH_2$—$S(O_2)$— and $Z_1$—NH—S$(O_2)$—, wherein $Z_1$ and $Z_2$ are independently selected from the group consisting of trifluomethyl, pentafluoroethyl, alkyl of 1 to about 12 carbon atoms, aryl of about 6 to about 14 carbon atoms, and aralkyl of about 6 to about 15 carbon atoms.

Especially preferred compounds include those wherein X is —C(=O)— or —$S(O_2)$—.

Especially preferred compounds include those wherein $R_1$ is an alkyl of about 5 to about 10 carbon atoms, alkyl of 1 to about 3 carbon atoms substituted with cyclic alkyl of about 5 to about 8 carbon atoms, aryl of about 6 to about 14 carbon atoms which is optionally mono-substituted with $Y_1$ or optionally di-substituted with $Y_1$ and $Y_2$, aralkyl of about 6 to about 15 carbon atoms which is optionally mono-substituted with $Y_1$ or optionally di-substituted with $Y_1$ and $Y_2$,

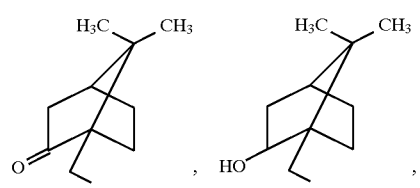

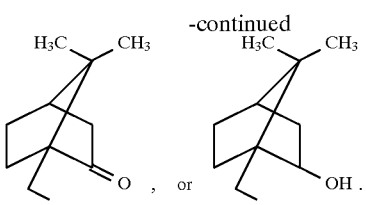

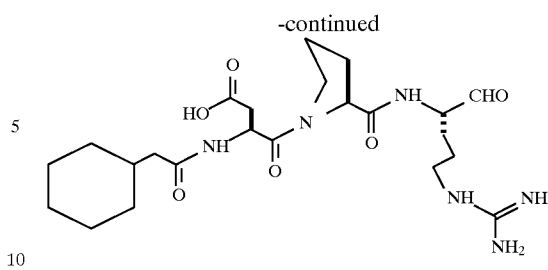

Suitable alkyl groups include methyl, ethyl, propyl, 1,1-dimethylethyl, 2-methylpropyl, 2,2-dimethylpropyl, butyl, 3-methylbutyl, 1-propylbutyl, pentyl, hexyl, cyclopentyl, cyclopentylmethyl, cyclohexyl, cyclohexylmethyl, adamantyl and adamantylmethyl. Suitable cyclic alkyls include cyclopentyl, cyclopentylmethyl, cyclohexyl, cyclohexylmethyl, adamantyl and adamantylmethyl. Suitable aryl groups include phenyl, naphthyl, biphenyl, 2-thienyl, 2-pyrrolyl and 2-furyl. Suitable aralkyl groups include phenylmethyl, diphenylmethyl, biphenyl, biphenylmethyl, naphthyl, naphthylmethyl, α-phenylmethylphenyl and 2-phenylethylene.

More especially preferred compounds include those wherein $R_1$ is 3-methylbutyl, 4-heptyl, 2-cyclohexylethyl, 2-phenylethyl and 1-naphthylmethyl, when X is —C(=O)—. Alternatively, more especially preferred compounds include those wherein $R_1$ is butyl, 4-methylphenyl, benzyl, naphthyl,

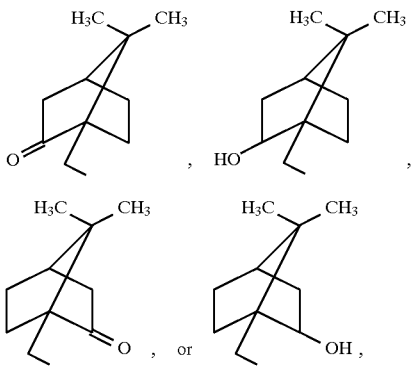

when X is —S(O$_2$)—.

The preferred compounds of formula (IA) include:

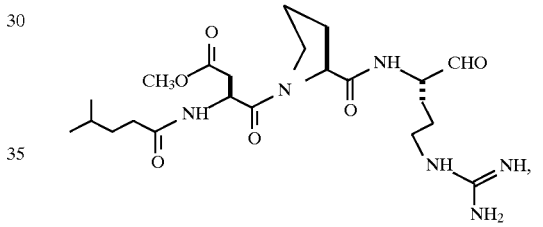

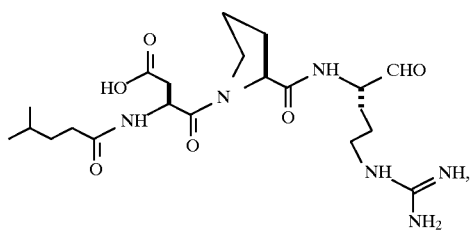

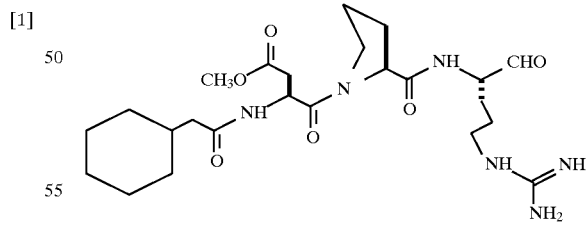

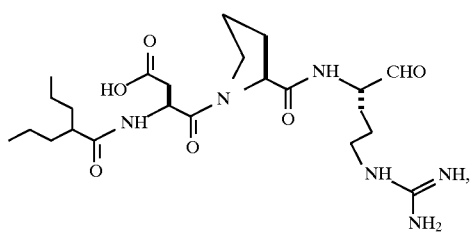

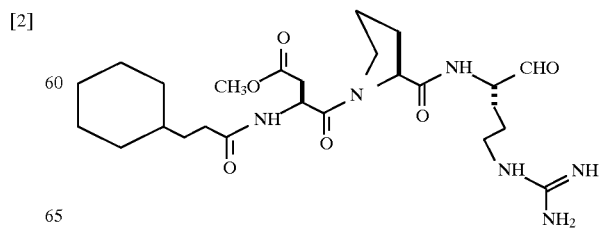

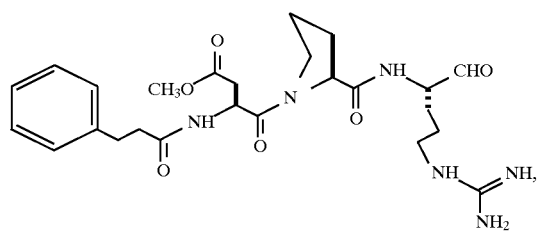
[10]
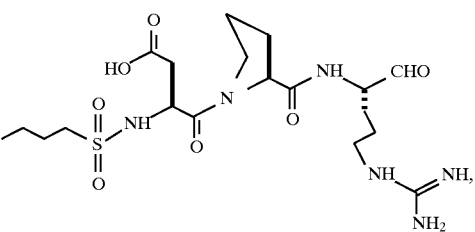
[16]
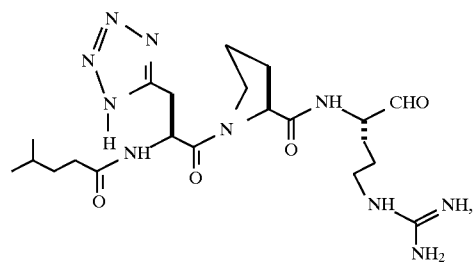
[11]
[17]
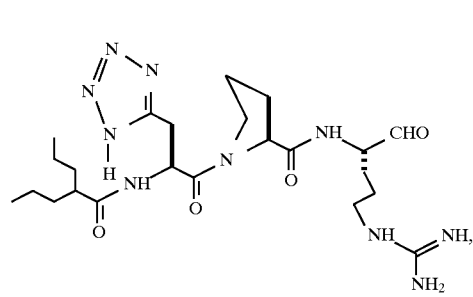
[12]
[18]
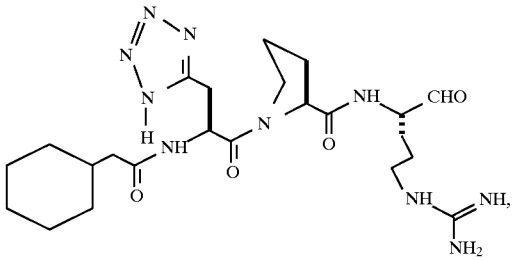
[13]
[19]
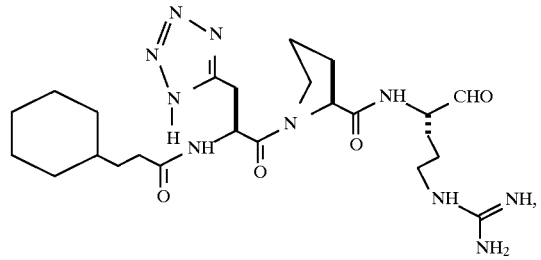
[14]
[20]
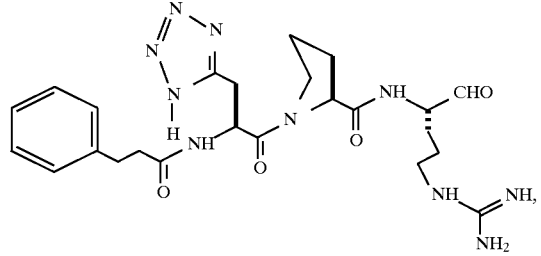
[15]
[21]

-continued
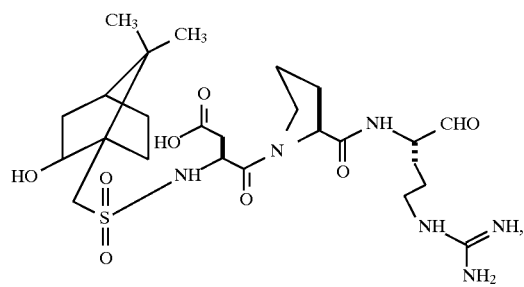
[22]
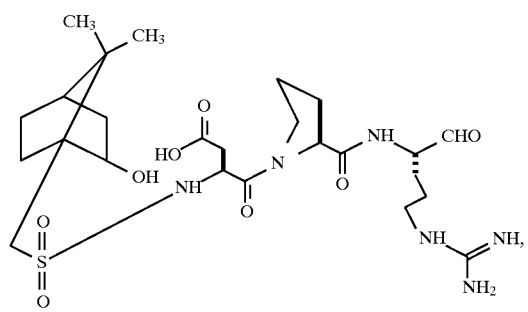
[23]
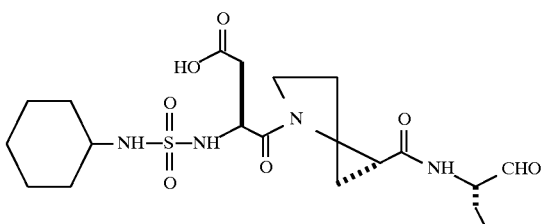
[24]
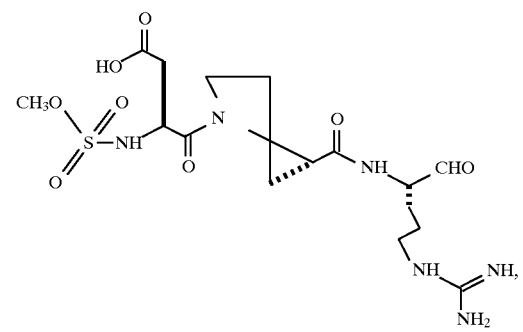
[25]
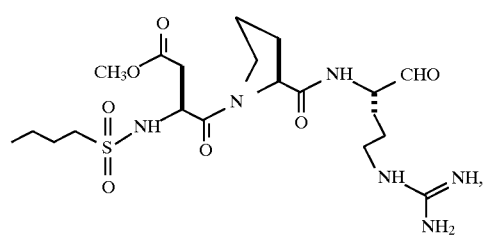
[26]
-continued
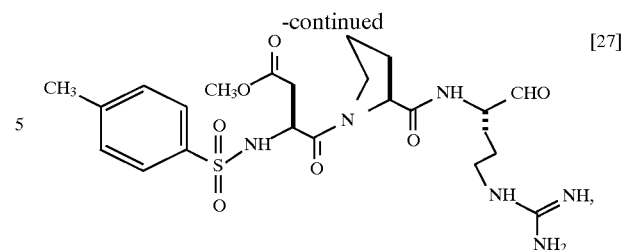
[27]
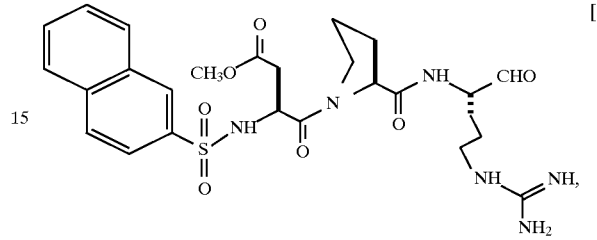
[28]
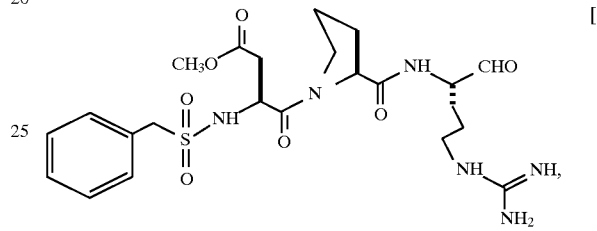
[29]
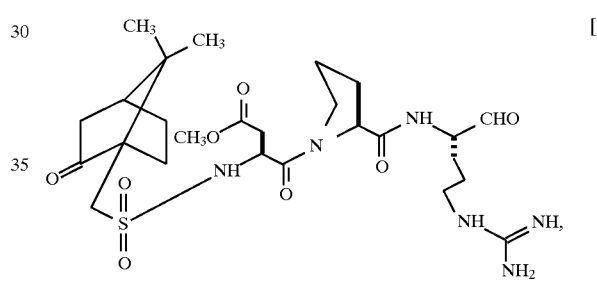
[30]
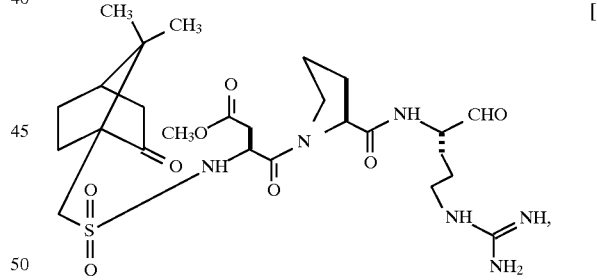
[31]
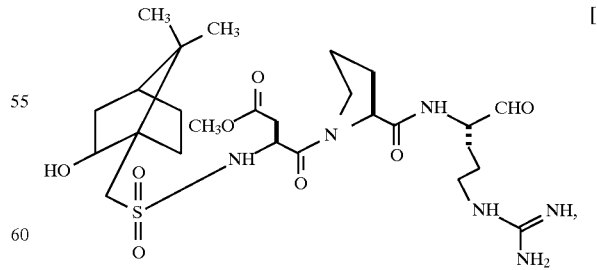
[32]

-continued
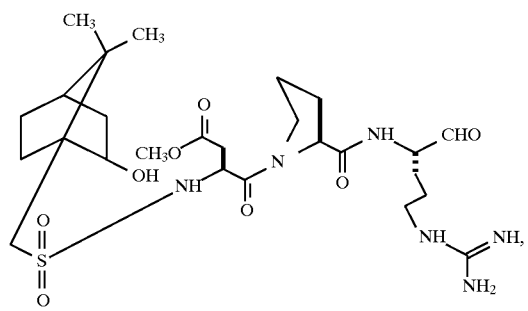
[33]
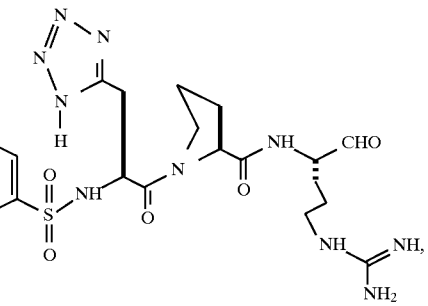
[38]
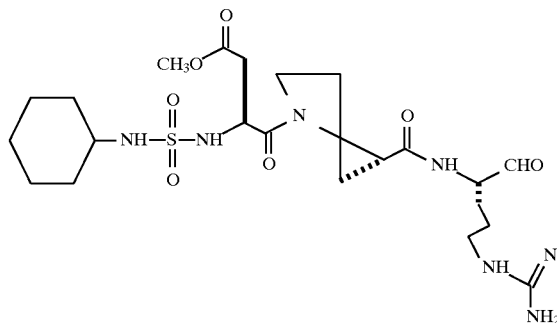
[34]
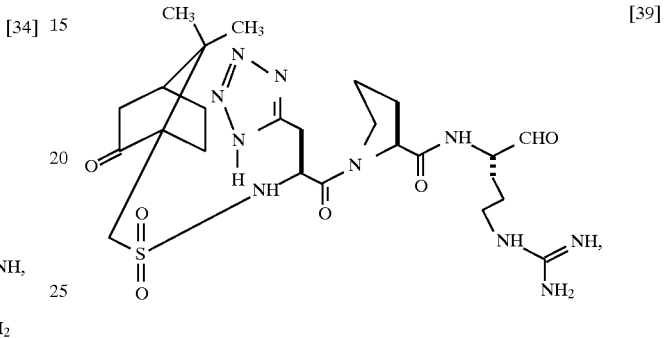
[39]
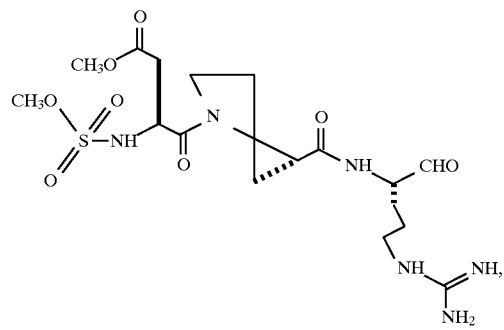
[35]
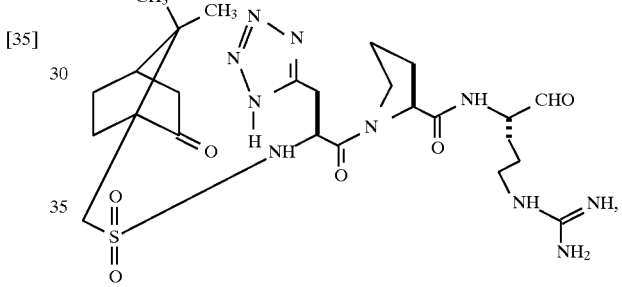
[40]
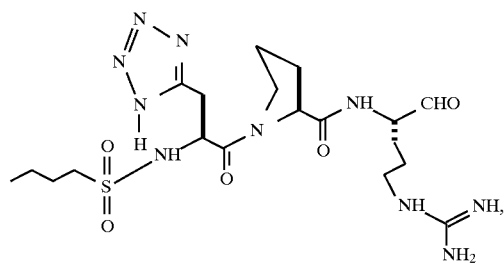
[36]
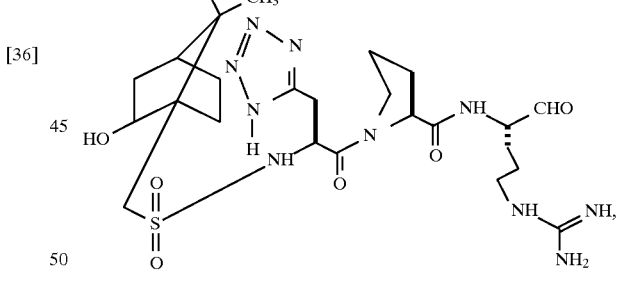
[41]
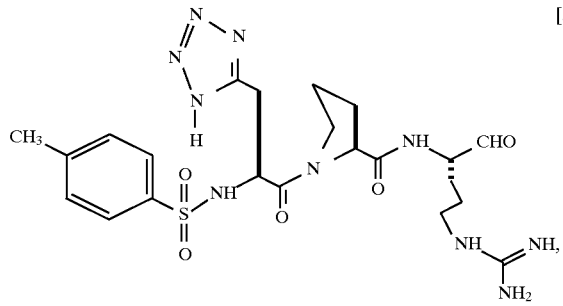
[37]
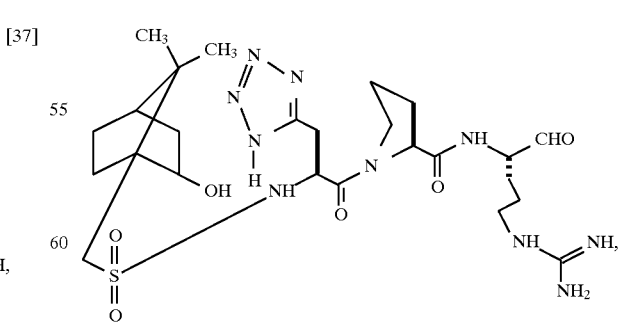
[42]

-continued

[43]
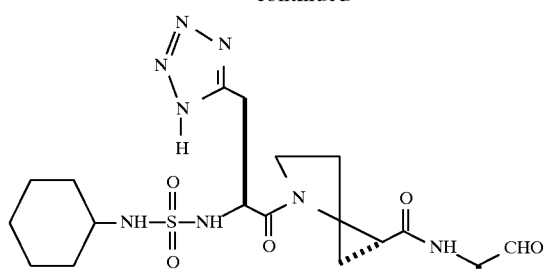

and

[44]
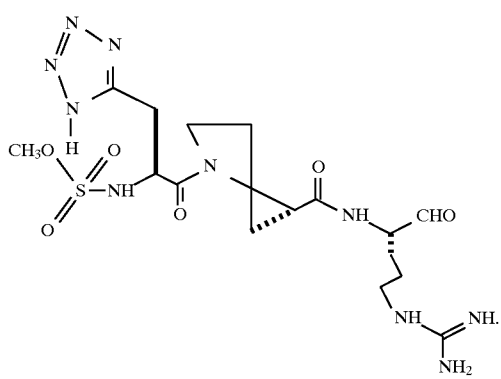

Especially preferred compounds of formula (I) include:

[2]
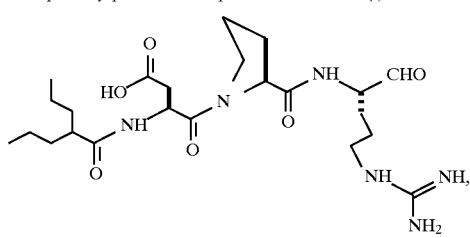

[7]
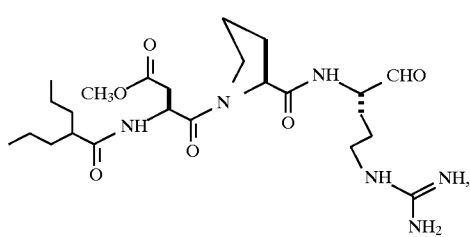

[12]
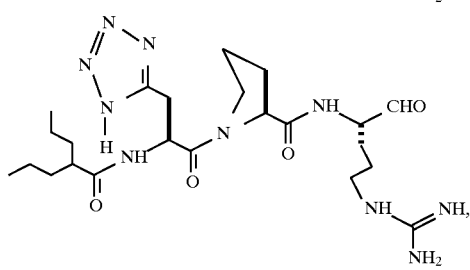

-continued

[11]
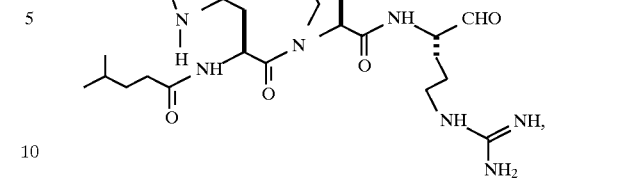

[14]
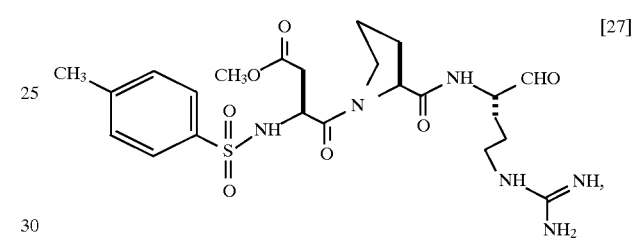

[27]
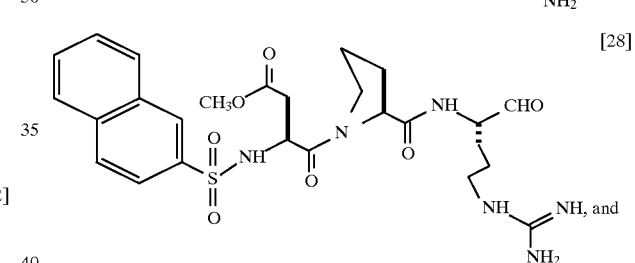

[28]
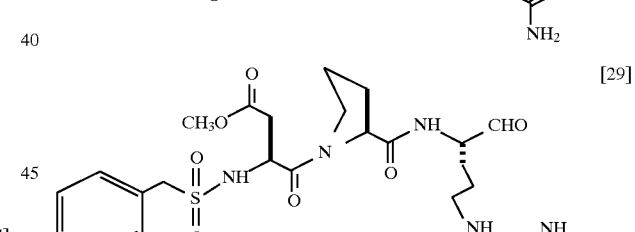

and

[29]
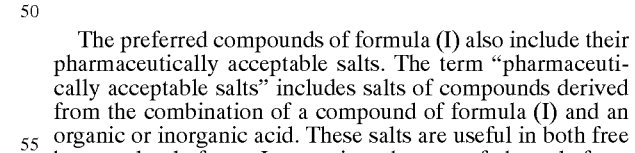

The preferred compounds of formula (I) also include their pharmaceutically acceptable salts. The term "pharmaceutically acceptable salts" includes salts of compounds derived from the combination of a compound of formula (I) and an organic or inorganic acid. These salts are useful in both free base and salt form. In practice, the use of the salt form amounts to use of the base form; both forms are within the scope of the present invention.

Preparation of Preferred Compounds

The peptide aldehyde derivatives of the present invention may be synthesized by either solid or liquid phase methods. Under certain conditions, the liquid phase method disclosed herein is preferred.

The starting materials used in either of these methods are readily available from chemical vendors as Aldrich, Sigma, Nova Biochemicals and the like.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (E. Gross & Meienhofer edit. 1981) and Vol. 9 (S. Udenfriend & J. Meienhofer edit. 1987), the disclosure of which are incorporated herein by reference.

The peptide aldehyde derivatives of the present invention may be synthesized by procedures described in the literature (see below) or by sequential chemical attachment of amino acid derivatives using the solid phase synthesis reagents and methods disclosed in the commonly assigned U.S. patent application of Webb, Ser. No. 07/807,474, filed Dec. 13, 1991, the disclosure of which is incorporated herein by reference.

FIG. 1 illustrates the synthesis of a solid phase reagent to which amino acid derivatives are later attached in the solid phase synthesis method. As shown in Example 8, intermediates to compounds of the present invention may be removed from the solid phase by treatment with formaldehyde in TFA and then deprotected by hydrogenation over Pd on carbon to give the compounds of the present invention.

Alternatively, as shown in Examples 14 and 15, the compound of the present invention may be removed from the solid phase in the form of a deprotected semicarbazone by treatment with HF/anisole, then transformed to the compound of the present invention by treatment of the semicarbazone with formaldehyde in dilute aqueous HCl.

Figure 2:
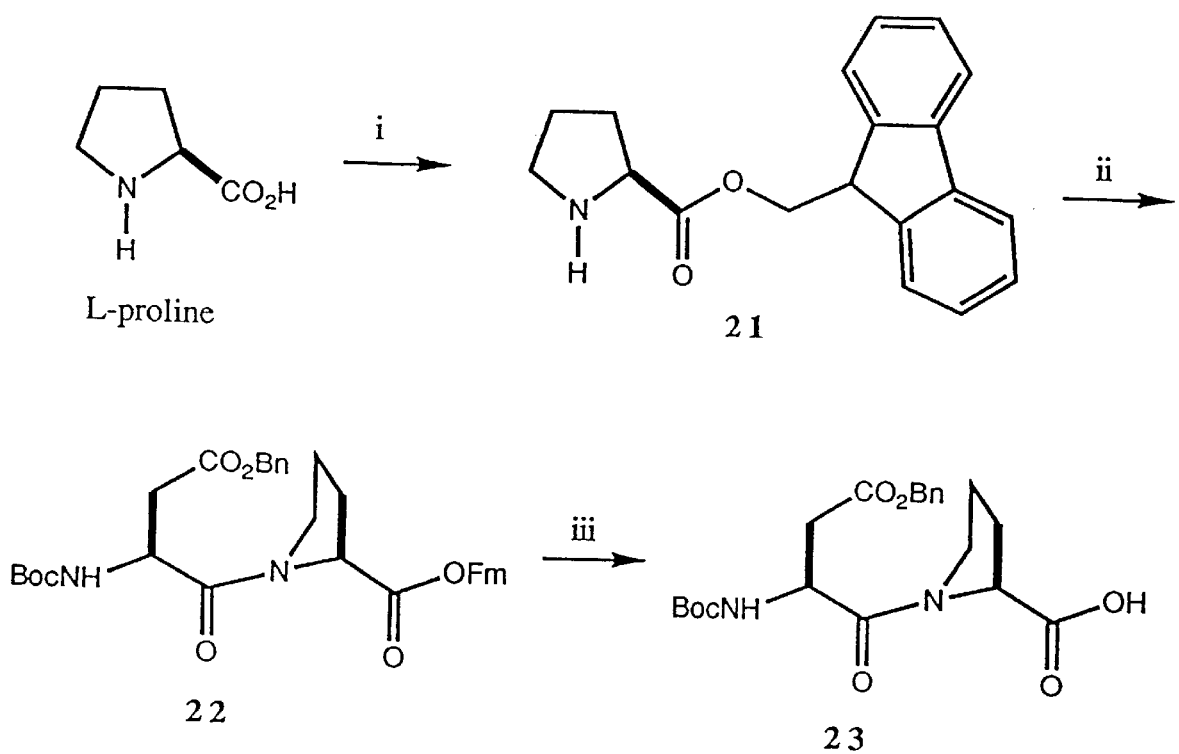
FIG. 2 depicts a reaction scheme describing a process for synthesis of a compound which may subsequently used to make one or more of the compounds of the present invention. In this figure, "i" refers to pTsOH/FmOH, toulene/reflux; "ii" Boc-Asp-β-benzyl ester/BOP/NMM/DMF; and "iii" refers to triethylamine/reflux.
Figure 3:
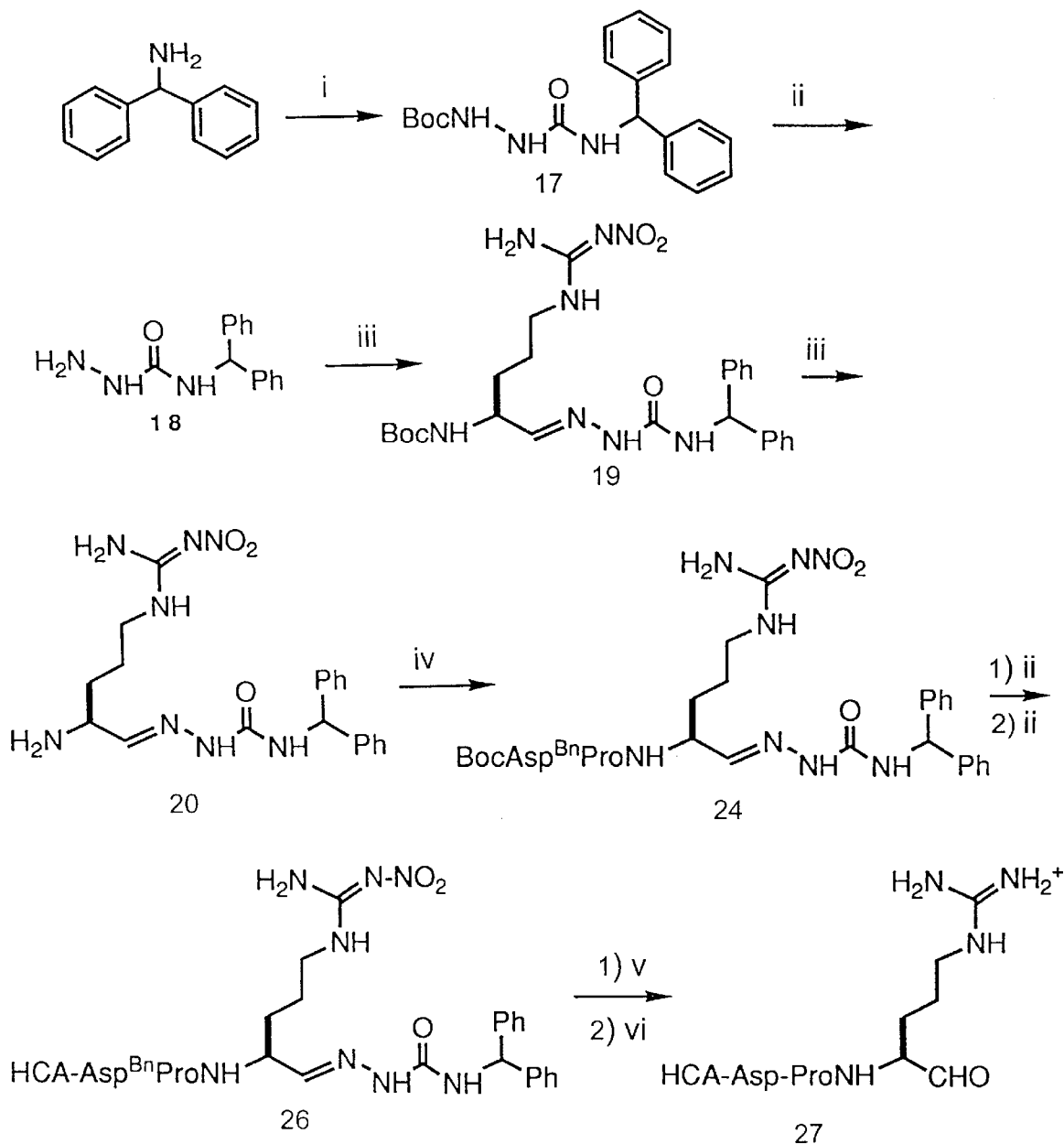
FIG. 3 depicts a reaction scheme describing a process for synthesis of one compound of the present invention by a liquid-phase method. In this figure, "i" refers to CDI and t-butylcarbazate; "ii" refers to TFA/DCM; "iii" refers to 1/NaOAc; "iv" refers to protected peptide (or analog) as the free acid (e.g., 23 of FIG. 2)/BOP/NMM/DMF; "v" refers to $H_2$/Pd; "vi" refers to $H_3O^+$; and "vii" refers to trimethylacetic acid/DCC/1-hydroxybenzotriazole/DMF. Alternatively "v" can refer to HF/anisole and "vi" can refer to formaldehyde/$H_3O^+$.

The peptide aldehydes of the present invention may also be synthesized by solution phase methods. Preferred is the method outlined in FIGS. 2 and 3. FIG. 2 depicts a process for the synthesis of a compound which is subsequently used to prepare the compounds of the present invention. FIG. 3 depicts a preferred process for the solution phase synthesis of the compounds of the present invention. Other methods for the solution synthesis of peptide aldehydes have been reported. For example, see McConnell et al., supra; at 87 and references therein; Bajusz et al., J. Med. Chem., 33: 1729 (1990); Kawamura et al., Chem. Pharm. Bull., 17: 1902 (1969), and Someno et al., Chem. Pharm. Bull., 34: 1748 (1986).

Selection of Preferred Compounds

The compounds of the present invention are distinguished by their ability to inhibit either thrombin or factor Xa, while not substantially inhibiting plasmin. The preferred compounds of the present invention may be selected as set forth below.

The compounds of the present invention are dissolved in buffer to give solutions containing concentrations such that assay concentrations range from 0 to 100 $\mu$M. In the assays for thrombin, factor Xa and plasmin, a chromogenic synthetic substrate is added to a solution containing test compound and the enzyme of interest and the residual catalytic activity of that enzyme is determined spectrophometrically. The $IC_{50}$ of compound is determined from the substrate turnover. $IC_{50}$ is that concentration of test compound giving 50% inhibition of the substrate turnover. Example A provides an exemplar of the in vitro assays used to select the compounds of the present invention.

The compounds of the present invention will preferably have an $IC_{50}$ of about 200 nM, in either the thrombin or factor Xa assay, and preferably the $IC_{50}$ for plasmin will not be less than the smaller of the $IC_{50}$ for thrombin or factor Xa. Preferred are compounds having an $IC_{50}$ of about 100 nM or less in either the thrombin or factor Xa assay or both assays.

Pharmaceutical Compositions

In another aspect, the present invention encompasses compositions prepared for storage or administration which comprise a therapeutically effective amount of the compounds of the present invention in a pharmaceutically acceptable carrier or diluent.

The "therapeutically effective amount" of the compound of the present invention will depend on the route of administration, the type of mammal being treated, and the physical characteristics of the specific mammal under consideration. These factors and their relationship to determining this dose are well known to skilled practitioners in the medical arts. This dose and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers or diluents" for therapeutic use are well known in the pharmaceutical art, and are described, for example, in *Remington's Pharmaceutical Sciences*, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. id. at 1449. In addition, antioxidants and suspending agents may be used. Id.

The pharmaceutical compositions of the present invention may be formulated and used as tablets, capsules or elixers for oral administration; suppositories for rectal administration; sterile solutions, suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

Utility and Methods

Compounds of the present invention when selected as disclosed are believed to be useful as potent inhibitors of thrombin and thrombin generation (from the direct inhibition of factor Xa), as well as for preventing or treating a condition characterized by abnormal thrombosis.

The compounds of the present invention are thought to be useful as in vitro diagnostic reagents for inhibiting clotting in blood drawing tubes. The use of stoppered test tubes having vacuum therein as a means to draw blood obtained by venipuncture into the tube is well known in the medical arts. Kasten, B. L., "Specimen Collection", *Laboratory Test Handbook,* 2nd Edition, Lexi-Comp Inc., Cleveland pp. 16–17 (Edits. Jacobs, D. S. et al. 1990). Such vacuum tubes may be free of clot-inhibiting additives, in which case, they would be useful for the isolation of mammalian serum from the blood. They may alternatively contain clot-inhibiting additives (such as heparin salts, EDTA salts, citrate salts or oxalate salt), in which case, they would be useful for the isolation of mammalian plasma from the blood. The compounds of the present invention are potent inhibitors of factor Xa or thrombin, and as such, can act be incorporated into blood collection tubes to prevent clotting of the mammalian blood drawn into them.

The compounds of the present invention can be used alone, in combination of other compounds of the present invention, or in combination with other known inhibitors of clotting, to the blood collection tubes. The amount to be added to such tubes would be that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are be added to blood collection tubes in such amounts that when combined with 2 to 10 mL of mammalian blood the concentration of such compounds will be sufficient to inhibit clot formation. Typically, the required concentration will be about 1 to 1000 nM, with 10 to 100 nM being preferred.

The present invention also includes methods for preventing or treating a condition in a mammal characterized by abnormal thrombosis, comprising administering to said mammal a therapeutically effective amount of a compound or a pharmaceutical composition of the present invention.

The "therapeutically effective amount" of the composition required as a dose will depend on the route of administration, the type of mammal being treated, and the physical characteristics of the specific mammal under consideration. These factors and their relationship to determining this dose are well known to skilled practitioners in the medical arts.

The "conditions characterized by abnormal thrombosis" would include those involving the arterial and venous vasculature. With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

In practicing the methods of the invention, the compounds or compositions can be used alone or in combination with one another, or in combination with other therapeutic or diagnostic agents. These compounds can be utilized in vivo, ordinarily in a mammal, preferably in a human, or in vitro.

In employing them in vivo, the compounds or compositions can be administered to a mammal in a variety of ways, including parenterally, intravenously, subcutaneously, intramuscularly, colonically, rectally, nasally or intraperitoneally, employing a variety of dosage forms. As will be apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

The dosage for the compounds of the present invention can range broadly depending upon the desired affects and the therapeutic indication. Typically, dosages will be between about 0.01 mg/kg and 100 mg/kg body weight, preferably between about 0.01 and 10 mg/kg, body weight. Administration is preferably parenteral, such as intravenous on a daily basis.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the invention as described herein and hereinafter claimed.

The invention will now be further illustrated by the following examples. The first seven examples are illustrated in FIG. 1.

EXAMPLES

Example 1

Preparation of α-N-t-butoxycarbonyl-N$^g$-nitroargininal

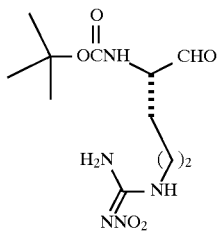

[50]

A. Procedure 1

The following procedure for the synthesis of α-t-butoxycarbonyl-N$^g$-nitro-argininal, the title compound, is an example of a general procedure for the preparation of Boc-amino acid aldehydes, see Patel et al., Biochim. Biophys. Acta, 748, 321–330 (1983). In 200 mL dry THF, 12.7 g Boc-N$^g$-nitro-arginine (40 mmoles) and 7.0 g carbonyldiimidazole (CDI; 43 mmoles) were added at room temperature and allowed to stir for 30 minutes. The reaction mixture was cooled to −78° C. and 35 mL of a solution of LiAlH$_4$ (1M in THF) were added dropwise over thirty minutes. The reaction was allowed to stir for an additional hour at −78° C. Next, 18 mL of acetone were added and this mixture was quickly added to 400 mL of 1N HCl. The mixture was extracted twice with 100 mL of ethyl acetate. The ethyl acetate washes were combined and then washed two times each with 100 mL water, 100 mL saturated NaHCO$_3$ and 100 mL saturated NaCl. The solution was dried (MgSO$_4$) and concentrated to a foam. The crude weight of the α-t-butoxycarbonyl-N$^g$-nitro-argininal was 6.36 g (21 mmole; yield 52%).

B. Procedure 2

Alternatively, the title compound was synthesized by a modification of the procedure of Fehrentz, J. A. and Castro, B., Synthesis, 676 (1983).

11.4 mL of N-methyl piperidine was slowly added to a stirred suspension of 8.42 g (94 mmole) of N,O-dimethylhydroxylamine in 75 mL dichloromethane which had been cooled to about 0° C. The solution was allowed to stir for 20 minutes which gave the free hydroxylamine, then was kept cold for use in the next step.

In a separate flask, 30.0 g (94 mmole) of Boc-N$^g$-nitroarginine was dissolved by heating in about 1400 mL of tetrahydrofuran, then the mixture was cooled under nitrogen to 0° C. 11.4 mL of N-methylpiperidine and 12.14 mL (94 mmole) of isobutylchloroformate was added and the mixture stirred for 10 minutes. The free hydroxylamine prepared above was added all at once and the reaction mixture was allowed to warm to room temperature, then stirred overnight.

The resulting precipitate was filtered off, then washed with 200 mL of tetrahydrofuran. After concentrating the filtrates to about 150 mL under vacuum, 200 mL of ethyl acetate was added, followed by ice to cool the solution. The cooled ethyl acetate phase was washed with two 75 mL portions of 0.2N hydrochloric acid, two 75 mL portions of 0.5N sodium hydroxide, one portion of 75 mL of brine, then the organic phase was dried over anhydrous magnesium sulfate. Upon concentration in vacuum, 22.7 g (70% yield) of solid Boc-N$^g$-nitroarginine N-methyl-O-methylcarboxamide was recovered. Thin layer chromatographic analysis in 9:1 dichloromethane/methanol (silica gel) showed one spot.

A flask was placed under a nitrogen atmosphere and cooled to −50° C., then charged with 70 mL (70 mmole) of 1N lithium aluminum hydride (in tetrahydrofuran) and 500 mL of dry tetrahydrofuran. 50 mL of a solution containing 66 mmole of Boc-N$^g$-nitroarginine N-methyl-O-methylcarboxamide in dry tetrahydrofuran was slowly added while the temperature of the reaction mixture was maintained at −50° C. After allowing the reaction mixture to warm to 0° C. by removal of the cooling, it was recooled to −30° C., at which temperature, 100 mL (0.2 mole) of 2N potassium bisulfate was added with stirring over about a 10 to 15 minute period. The reaction mixture was then allowed to stir at room temperature for 2 hours. After filtering off the precipitate, the filtrate was concentrated to 100 mL under vacuum. The concentrate was poured into 800 mL ethyl acetate, then was successively washed with two 50 mL portions of 1N hydrochloric acid, two 50 mL portions of saturated sodium bicarbonate, one 50 mL portion of brine. The combined aqueous extracts were extracted with 3–100 mL portions of ethyl acetate. All of the ethyl acetate washes were combined, then was dried over anhydrous magnesium sulfate. The mixture was concentrated under vacuum to yield 18.5 g (95%) of the title compound.

Example 2

Preparation of trans-4-(aminomethyl)-cyclohexane carboxylic acid benzyl ester para-touluenesulfonate salt

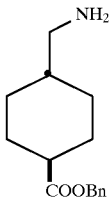

[51]

50 g (0.318 moles) of trans-4-(aminomethyl)-cyclohexane carboxylic acid, 61.7 g (0.324 moles) p-toluenesulfonic acid, 250 mL (2.4 moles) benzyl alcohol and 250 mL toluene were combined and stirred. The mixture was refluxed for 24 hours and the liberated water was removed azeotropically by means of a Dean and Stark apparatus. A clear solution was obtained after 5 hours of refluxing. The solution was allowed to cool to room temp. and the product crystallized. The mixture was vacuum filtered, washed with ether and dried in a vacuum oven to give 128.12 g (96% yield.) Reference: Greenstein, Jesse P.; Winitz, Milton. *Chemistry of the Amino Acids.* vol. 2, (1986), 942. $^1$H NMR (CD$_3$OD) δ1.05 (m, 2H), 1.43 (m, 2H), 1.59 (m, 1H), 1.85 (m, 2H), 2.03 (m, 2H), 2.33 (m, 1H), 2.35 (s, 3H), 2.75 (d, 2H), 5.09 (s, 2H), 7.23 (d, 2H), 7.32 (m, 5H), 7.69 (d, 2H). M.P. 154°–156° C.

Example 3

Preparation of 1-t-butoxycarbonyl-semicarbazidyl-trans-4-methyl cyclohexane carboxylic acid benzyl ester

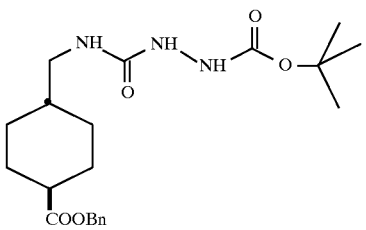

[52]

3.24 g (0.02 moles) carbonyldiimidazole (CDI) were dissolved in 45 mL of dimethylformamide (DMF) at room temperature under nitrogen. A solution of 2.48 g (0.02 moles) t-butyl carbazate in 45 mL DMF was added dropwise. Next 8.38 g (0.02 moles) of solid benzyl ester of Example 2 was added, followed by the dropwise addition of 3.06 mL of triethylamine (TEA) over a 30 min. period. The reaction was allowed to stir at room temperature under nitrogen for one hour. Water (100 mL) was added and this mixture was extracted three times with 50 mL of ethyl acetate. The ethyl acetate layers were combined and extracted two times each with 75 mL 1N HCl, H$_2$O, NaHCO$_3$, NaCl and dried with MgSO$_4$. The mixture was filtered and the solution was concentrated to give an oil. This material could be purified by recrystallization from ethyl acetate/hexanes (M.P.=106°–108° C.) or used directly in the next step. $^1$H NMR (CDCl$_3$) δ0.94 (m, 2H), 1.42 (m, 2H), 1.45 (s, 9H), 1.81 (m, 2H), 2.02 (m, 2H), 2.27 (m, 1H), 3.17 (t, 2H), 5.09 (s, 2H), 5.51 (t, 1H), 6.46 (s, 2H), 7.34 (m, 4H).

Example 4

Preparation of 1-(t-butoxycarbonyl)-3-semicarbazidyl-trans-4-methyl-cyclohexane carboxylic acid

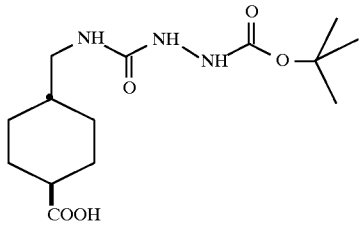

[53]

To the crude Boc-benzyl ester of Example 3 from above, 250 mL of methanol (MeOH) and 500 mg of 10% palladium on activated carbon were added. After shaking on the hydrogenator for one hour at 5 psi, the mixture was filtered with Celite through a fine fritted filter. The solution was concentrated to a foam, methylene chloride was added and a precipitate formed. The mixture was kept 5° C. for 65 hours. The crystallized material was filtered with ether and 4.0 g of crude product were obtained (12.7 mmoles; yield 62% overall yield from the compound of Example 2) $^1$H NMR (CD$_3$OD), δ0.96, (m, 2H), 1.42 (m, 2H), 1.46 (S, 9H), 1.82 (m, 2H), 1.97 (m, 2H), 2.18 (m, 1H), 3.0 (t, 2H). M.P.=185°–189° C.

Example 5

Preparation of semicarbazidyl-trans-4-methyl cyclohexane carboxylic acid trifluoroacetate salt

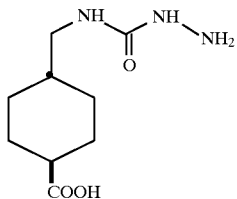

[54]

315 mg (1 mmole) of compound of Example 4 was added to 10 mL of trifluoroacetic acid (TFA) at 0° C. and the resulting solution was allowed to stir for 30 min. After this time the solution was added dropwise to 75 mL of ether. A precipitate formed, and the mixture was filtered and washed with ether. Weight of crude product was 254 mg, 0.77 mmoles; yield (77%). $^1$H NMR (CD$_3$OD), δ1.0 (m, 2H), 1.38 (m, 2H), 1.43 (m, 1H), 1.84 (m, 2H), 2.01 (m, 2H), 2.22 (m, 1H), 3.04 (d, 2H). M.P.=154°–156° C.

Example 6

Preparation of α-(t-butoxycarbonyl)-N$^g$-nitro argininal-semicarbazonyl-trans-4-methyl-cyclohexane carboxylic acid

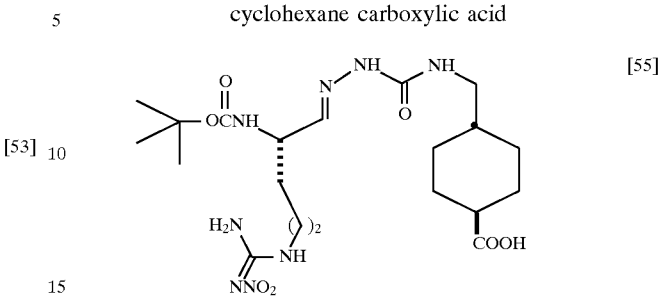

[55]

A solution of 13.7 g (41.6 mmoles) of the compound of Example 5, 18.0 g (~59 mmoles) of crude compound of Example 1 in 135 mL ethanol containing 45 mL of water, was treated with 9.41 g (69 mmoles) of sodium acetate (NaOAc) and refluxed for one hour. This solution was allowed to cool and then poured into 0.1N HCl and extracted three times with ethyl acetate. The combined organic phase was washed with water, then brine, dried (MgSO$_4$) and concentrated to a small volume. This cloudy mixture was allowed to set overnight at 5° C. to precipitate the product, which was isolated by filtration and dried under vacuum. This gave 9.9 g, 47% yield based on the amount of the compound of Example 5 used. $^1$H NMR (CD$_3$OD) δ1.0 (m, 2H), 1.43 (s, 9H), 1.45–2.20 (m, 13H), 3.09 (d, 2H), 3.30 (m, 2H), 4.18 (bs, 1H), 7.10 (d, 1H). M.P.=162°–163° C.

Example 7

Synthesis of Semicarbazone Solid Phase

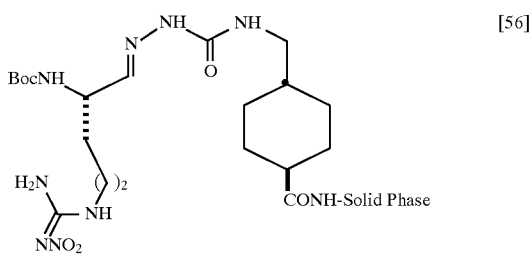

[56]

The title resin, a solid phase reagent, was prepared by placing 0.8 g (0.5 mmoles, 0.62 g/mole) methylbenzhydralamine (MBHA) resin in a reaction vessel and washing one time with dichloromethane (DCM) (all washes require 10 mL of solvent with agitation for 1 to 2 minutes), three times with dimethylformamide (DMF), two times with 10% diisopropylethylamine(DIEA)/DMF, and four times with DMF. 5 mL DMF, 1 mmole (102 µL) 4-methylmorpholine, 1 mmole (443 mg) benzotriazol-1-yloxy-tris-(dimethylamino)-phosphonium-hexafluorophosphate (BOP reagent) and 1 mmole (500 mg) of the compound of Example 6 were added, mixed on a rotating wheel for 16 hours, and washed three times with DMF, two times with 10% DIEA/DMF and three times with DMF. The resin was then washed successively with DCM, methanol and ether. The title resin showed a 98–99% coupling yield by ninhydrin.

This resin was then extended at the N-terminus, with amino acids or amino acid analogs, on a conventional peptide synthesizer using standard t-Boc methodology as shown in the examples which follow.

The synthesis of the peptide analogs was performed on an Applied Biosystems Model 430A peptide synthesizer using the t-Boc chemistry conditions in the 430A user's manual. The resulting protected peptide aldehyde can be cleaved from the support with formaldehyde and deprotected with hydrogen/Pd. The nitro group can be removed from the guanidine group without reduction of the aldehyde.

Example 8

Preparation of N-(4-methylpentanoyl)-L-aspartyl-L-prolyl-L-argininal

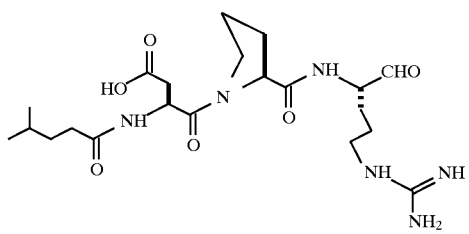

[1]

The title compound was synthesized using an Applied Biosystems Model 430A peptide synthesizer. The Boc chemistry conditions utilized were as provided in the instrument user's manual.

0.500 g of resin of Example 7 was made ready for use by removing the Boc protecting groups by treatment with 50% trifluoroacetic acid (in dichloromethane). After washing and neutralizing the acidity by treatment with 10% diisopropylethylamine (in dichloromethane), commercially available Boc-protected amino acids were coupled to the support reagent (and the growing amino acid support chain) in a sequential manner.

Thus, N-Boc-L-proline was attached to the resin using dicyclohexylcarbodiimide and 1-hydroxybenzotriazole in dimethylformamide, followed by treatment with 50% trifluoroacetic acid (in dichloromethane) to remove the Boc protecting group, a wash step and a wash with 10% diisopropylethylamine (in dichloromethane) to neutralize acidity. N-Boc-L-aspartic acid-β-benzyl ester was coupled and deprotected in the same manner. 4-methylvaleric acid was coupled to the peptide on the solid phase using dicyclohexylcarbodiimide and 1-hydroxybenzotriazole in dimethylformamide.

The peptide aldehyde was removed from the solid phase, by treatment with a mixture comprising 5 mL tetrahydrofuran, 1 mL acetic acid, 1 mL formaldehyde and 0.100 mL 1N HCl for 1 hour with stirring. After filtering this mixture, the resin was washed with 10 mL of tetrahydrofuran. The combined filtrates were diluted with 100 mL water and extracted with ethyl acetate. The ethyl acetate phase was then washed with saturated NaCl, dried over magnesium sulfate, and concentrated under vacuum.

To remove the nitro and benzyl protecting groups of the peptide aldehyde, the concentrated peptide aldehyde was taken up in a mixture of 10 mL of 10%, water in methanol, 0.300 mL 1N HCl and 0.200 g palladium on carbon, then treated with hydrogen at 5 psi for 45 minutes. The mixture was filtered through a fine fritted filter with Celite, washed with 10% water in methanol and concentrated to give the crude peptide aldehyde.

The resulting peptide aldehyde is then purified using reverse phase HPLC on a 10 micron particle size, 300 angstrom pore size C-18 column, eluting with a water-acetonitrile (both containing 0.1% trifluoroacetic acid) gradient, where the gradient ran from 5% to 40% acetonitrile. The column fractions were analyzed by analytical HPLC and fractions containing pure product were pooled and lyophilized to yield the title compound. Fast atom bombardment mass spectrometry confirmed the theoretical molecular weight of 468.3 a.m.u.

Example 9

Preparation of N-octanyl-L-aspartyl-L-prolyl-L-argininal

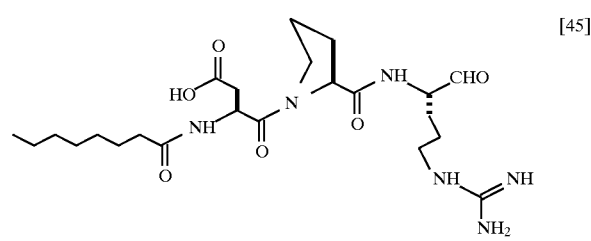

[45]

The title compound was synthesized and purified in the same manner as described in Example 8.

N-Boc-L-proline was first attached to resin of Example 7 followed by N-Boc-L-aspartic acid-p-benzyl ester. After treating with 50% trifluoroacetic acid (in dichloromethane) to remove the t-Boc protecting group, and washing to neutralize acidity, octanoic acid (in the place of 4-methylvaleric acid) was coupled to the peptide on the solid phase. The title compound was obtained after further deprotection and purification. Fast atom bombardment mass spectrometry confirmed the theoretical molecular weight of 496.3 a.m.u.

Example 10

Preparation of N-(3-phenylpropionyl)-L-aspartyl-L-prolyl-L-argininal

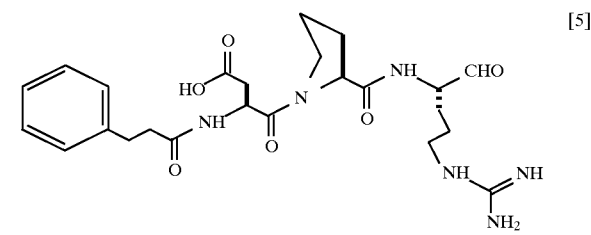

[5]

The title compound was synthesized and purified in the same manner as described in Example 8.

N-Boc-L-proline was first attached to resin of Example 7 followed by N-Boc-L-aspartic acid-β-benzyl ester. After treating with 50% trifluoroacetic acid (in dichloromethane) to remove the t-Boc protecting group, and washing to neutralize acidity, 3-phenylpropionic acid (in the place of 4-methylvaleric acid) was coupled to the peptide on the solid phase. The title compound was obtained after further deprotection and purification. Fast atom bombardment mass spectrometry confirmed the theoretical molecular weight of 502.3 a.m.u.

Example 11

Preparation of N-((±)-2-methyl-3-phenylpropionyl)-L-aspartyl-L-prolyl-L-argininal

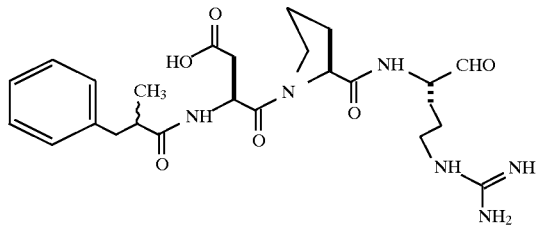

[46]

The title compound was synthesized and purified in the same manner as described in Example 8.

N-Boc-L-proline was first attached to resin of Example 7 followed by N-Boc-L-aspartic acid-β-benzyl ester. After treating with 50% trifluoroacetic acid (in dichloromethane) to remove the t-Boc protecting group, and washing to neutralize acidity, (±)-2-methyl-3-phenylpropionic acid (in the place of 4-methylvaleric acid) was coupled to the peptide on the solid phase. The title compound was obtained after further deprotection and purification. Fast atom bombardment mass spectrometry confirmed the theoretical molecular weight of 516.3 a.m.u.

Example 12

Preparation of N-(1-cyclohexylacetyl)-L-aspartyl-L-prolyl-L-argininal

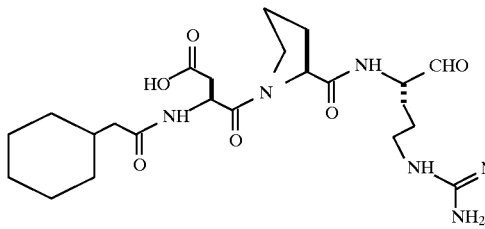

[3]

The title compound was synthesized and purified in the same manner as described in Example 8.

N-Boc-L-proline was first attached to resin of Example 7 followed by N-Boc-L-aspartic acid-β-benzyl ester. After treating with 50% trifluoroacetic acid (in dichloromethane) to remove the t-Boc protecting group, and washing to neutralize acidity, cyclohexane acetic acid (in the place of 4-methylvaleric acid) was coupled to the peptide on the solid phase. The title compound was obtained after further deprotection and purification. Fast atom bombardment mass spectrometry confirmed the theoretical molecular weight of 494.6 a.m.u.

Example 13

Preparation of N-(3-phenylpropionyl)-L-glutamyl-L-prolyl-L-argininal

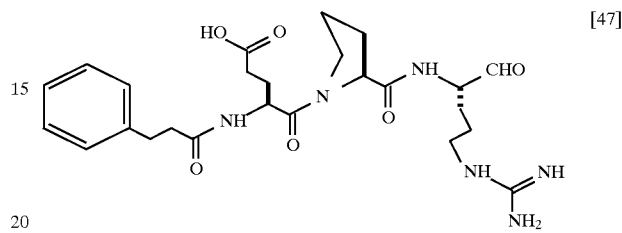

[47]

The title compound was synthesized and purified in the same manner as described in Example 8.

N-Boc-L-proline was first attached to resin of Example 7 followed by N-Boc-L-glutamic acid-β-benzyl ester (in the place of N-Boc-L-aspartic acid-β-benzyl ester). After treating with 50% trifluoroacetic acid (in dichloromethane) to remove the t-Boc protecting group, and washing to neutralize acidity, 3-phenylpropionic acid (in the place of 4-methylvaleric acid) was coupled to the peptide on the solid phase. The title compound was obtained after further deprotection and purification. Fast atom bombardment mass spectrometry confirmed the theoretical molecular weight of 516.3 a.m.u.

An alternative method of removing the intermediate of the compounds of the present invention from the solid phase will now be demonstrated in the Examples 14 and 15.

Example 14

N-(3-cyclohexanepropionyl)-L-aspartyl-L-prolyl-L-argininal-semicarbazonyl-trans-4-aminomethylcyclohexane carboxamide

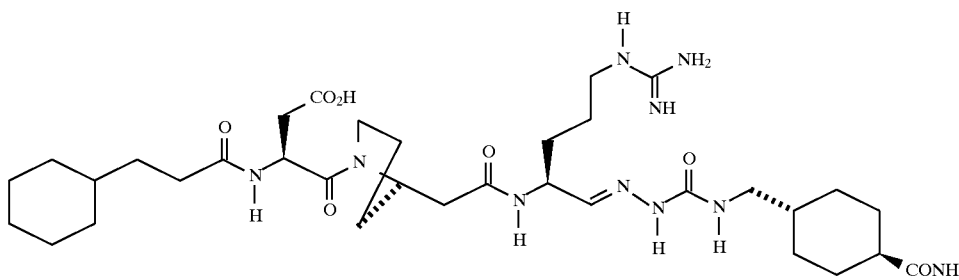

[57]

The title compound was synthesized on the resin of Example 7 in the same manner as described in Example 8. N-Boc-L-proline was first attached to resin of Example 7 followed by N-Boc-L-aspartic acid-β-benzyl ester. After treating with 50% trifluoroacetic acid (in dichloromethane) to remove the t-Boc protecting group, and washing to neutralize acidity, 3-cyclohexanepropionic acid (in the place of 4-methylvaleric acid) was coupled to the peptide on the solid phase.

300 mg of MBHA(methylbenzhydrylamine) resin-supported peptide was weighed out into a cyclindrical teflon reaction vessel. 300 μL of anisole was added and the reaction flash was attached to an HF apparatus via a screw thread. 3 mL of anhydrous HF was condensed into the flask at −20° C. The reaction mixture was magnetically stirred for 0.5 hours at −20° C., warmed to 0° C., and stirred for an additional 1 hour. The HF was removed under a stream of nitrogen and the crude product was extracted from the resin with 50 mL of 0.1M ammonium bicarbonate. This aqueous extract was washed with diethyl ether (3×25 ml), frozen, and lyophilized to yield the crude product as a white foam. This semicarbazone was purified using reverse phase HPLC on a 10 micron particle size, 300 angstrom pore size C-18 column, eluting with a water (containing 15 mM ammonium bicarbonate, pH=7.1)-acetonitrile gradient, where the gradient ran from 15% to 40% acetonitrile over 45 minutes. The column fractions were analyzed by analytical HPLC and fractions containing product (retention time=18 minutes) were pooled, frozen, and lyophilized to yield a white powder (60 mg, 0.085 mmol)

Example 15

N-(3-cyclohexanepropionyl)-L-aspartyl-L-prolyl-L-argininal

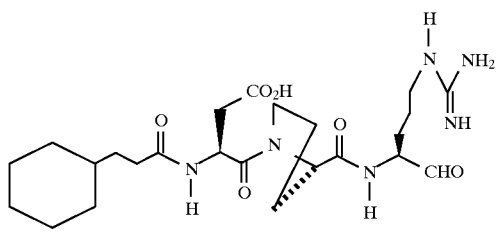

[4]

The semicarbazone of Example 14 (60 mg, 0.085 mmole) was treated with a mixture of 14.1 mL of aqueous TFA (buffered to pH=1) and 636 μL of 37% formaldehyde (8.5 mmols, 100 eq). This mixture was stirred for 0.5 hours at 23° C., filtered through a 0.2 μm filter, and purified using reverse phase HPLC on a 10 micron particle size, 300 angstrom pore size C-18 column, eluting with a water (containing 0.1% trifluoroacetic acid)-acetonitrile gradient, where the gradient ran from 10% to 30% acetonitrile over 45 minutes. The column fractions were analyzed by analytical HPLC and fractions containing product (retention time=17 minutes) were pooled to yield 20 mg (0.039 mmol) of product after lyophilization. Mass spectral analysis of this material revealed an M+1 peak at 509.2 amu.

Example 16

Preparation of N-(2-propylpentanoyl)-L-aspartyl-L-prolyl-L-argininal

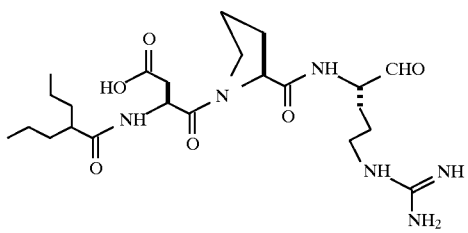

[2]

The title compound was synthesized, cleaved from the resin, deprotected and purified in the same manner as described in Examples 14 and 15.

N-Boc-L-proline was first attached to resin of Example 7 followed by N-Boc-L-aspartic acid-β-benzyl ester. After treating with 50% trifluoroacetic acid (in dichloromethane) to remove the t-Boc protecting group, and washing to neutralize acidity, 2-propylpentanoic acid (in the place of 4-methylvaleric acid) was coupled to the peptide on the solid phase. The title compound was obtained after further deprotection and purification. Fast atom bombardment mass spectrometry confirmed the theoretical molecular weight of 496.3 a.m.u.

The method of liquid phase synthesis of certain compounds of the present invention will now be demonstrated in examples 17 to 46.

Example 17

Preparation of 1-t-butoxycarbonyl-semicarbazidyl-4-diphenylmethane

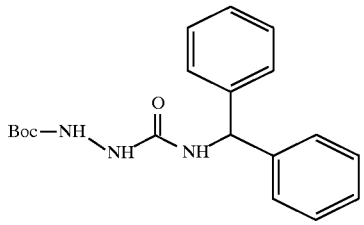

[58]

A solution of 16.2 g (0.10 mole) of carbonyldiimidazole (CDI) in 225 mL of dimethylformamide (DMF) was prepared at room temperature and allowed to stir under nitrogen. A solution of 13.2 g (0.100 moles) t-butyl carbazate in 225 mL DMF was then added dropwise over a 30 min. period. Next, 18.3 g (0.10 moles) of diphenylmethylamine in 100 mL of DMF was added over a 30 minute period. The reaction was allowed to stir at room temperature under nitrogen for one hour. Water (10 mL) was added and this mixture was concentrated to about 150 mL under vacuum. This solution was poured into 500 mL water and extracted with 400 mL of ethyl acetate. The ethyl acetate phase was extracted two times each with 75 mL 1N HCl, $H_2O$, saturated $NaHCO_3$, brine and dried with $MgSO_4$. The mixture was filtered and the solution was concentrated to give 29.5 g (85% yield) of the title compound as a white foam. This material could be purified by recrystallization from ethyl acetate/hexane, but was pure enough to use directly in the next step: mp 142°–143° C. Anal. Calcd. for $C_{19}H_{23}N_3O_3$: C, 66.84; H, 6.79; N, 12.31. Found: C, 66.46; H, 6.75; N; 12.90.

Example 18

Preparation of semicarbazidyl-4-diphenylmethane trifluoroacetate salt

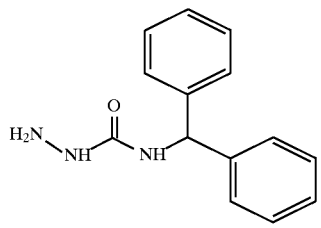

[59]

A solution of 3.43 g (10 mmole) of the compound of Example 17 in 12.5 mL of dichloromethane was treated with 12.5 mL of trifluoroacetic acid (TFA) at 0° C. and allowed to stir for 30 min at this temperature. After this time the solution was added dropwise to 75 mL of ether. A precipitate formed, and the mixture was filtered and washed with ether. Weight of the crude title compound was 2.7 g (80% yield): mp 182°–184° C.

Example 19

Preparation of α-N-(t-butoxycarbonyl)-N$^g$-nitro-argininal-semicarbazonyl-4-N-diphenylmethane

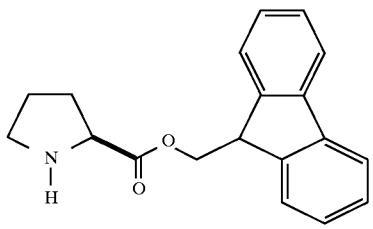

[60]

A solution of 2.65 g (7.8 mmoles) of the compound of Example 18 and 2.36 g (7.8 mmoles) of the compound of Example 1 (α-N-(t-butoxycarbonyl)-N$^g$-nitro-argininal) in 20 mL ethanol containing 6 mL of water, was treated with 1.2 g (8.8 mmoles) of sodium acetate and refluxed for one hour. This solution was allowed to cool and then poured into water and extracted three times with ethyl acetate. The combined organic phase was washed with water, 0.1N HCl, brine, dried (MgSO$_4$) and concentrated to a small volume. The white solid residue was recrystallized from acetonitrile/ether. This gave 3.2 g of the title compound (78% yield based on the compound of Example 18): mp 78°–79° C.

Example 20

Preparation of N$^g$-nitro-argininal-semicarbazonyl-4-N-diphenylmethane trifluoroacetate salt

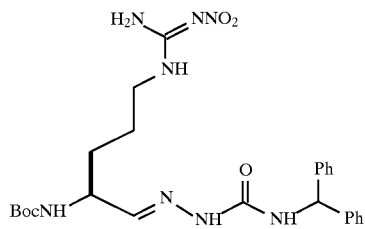

[61]

A solution of 0.53 g (1.0 mmole) of the compound of Example 19 in 5 mL of dichloromethane was treated with 5 mL of trifluoroacetic acid (TFA) at 0° C. and allowed to stir for 30 minutes at this temperature. After this time the solution was added dropwise to 40 mL of ether. A precipitate formed, and the mixture was filtered and washed with ether. This gave 0.51 g of the title compound as a pure white solid (97% yield): mp 159°–160° C.

Example 21

Preparation of L-proline-9-fluorenemethyl ester p-toluenesulfonic acid salt

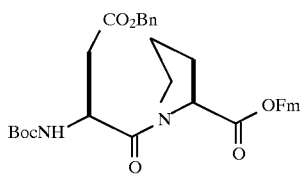

[62]

A solution of L-proline 15.99 g (139.0 mmole), 9-fluorenemethanol 30.0 g (152.9 mmole), and p-toluenesulfonic acid in 600 mL of toluene was refluxed and water was removed with a Dean-Stark trap. After 26 hours, the reaction was concentrated to give 64 g (99% crude yield) of an oil of the title compound which was used directly in the next step.

Example 22

Preparation of α-N-(t-butoxycarbonyl)-L-aspartyl-β-(benzylester)-L-proline-9-fluorenemethyl ester

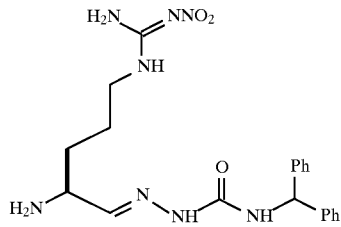

[63]

A solution of the compound of Example 21 (L-proline-9-fluorenemethyl ester p-toluenesulfonic acid salt) (15.44 g, 33.2 mmole), α-N-(t-butoxycarbonyl)-L-aspartic acid-β-(benzyl ester) (9.35 g, 41.9 mmole), benzotriazol-1-yloxy-tris-(dimethylamino)-phosphonium-hexafluorophosphate (BOP reagent) 18.6 g (42.0 mmole) in 100 mL DMF was allowed to stir in an ice-bath. This solution was treated with 1-hydroxybenzotriazole hydrate (0.45, 3.34 mmole), diisopropylethylamine (19.0 mL, 198 mmole) and the reaction allowed to stir at 0°–5° C. for 1.5 hours. After this time the reaction mix was poured into 600 mL of ethyl acetate and extracted successively with saturated aqueous citric acid, water, saturated sodium bicarbonate, and finally brine. The organic phase was dried (MgSO$_4$) and concentrated under vacuum to give 18 g (91% crude yield) of the title compound as an oil, which was used directly in the next step.

Example 23

Preparation of α-N-(t-butoxycarbonyl)-L-aspartyl-β-(benzyl ester)-L-proline

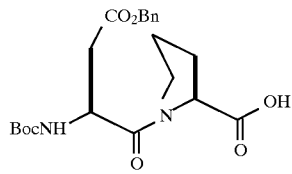
[64]

The crude oil from above, α-N-(t-butoxycarbonyl)-L-aspartyl-β-(benzyl ester)-L-proline-9-fluorenemethyl ester of Example 22 (17.5 g, 29.2 mmole) was suspended in 250 mL of triethylamine and allowed to reflux for 1 hour. This mixture was concentrated to an oil, dissolved in 600 mL of ethyl acetate The ethyl acetate phase was washed once with citric acid, once with brine, dried (MgSO$_4$) and conc. to give an oil. This material was purified by column chromatography (silica gel, 10–20% THF/DCM) to give 7.5 g (38% overall from the compound of 21).

Example 24

Preparation of α-N-(t-butoxycarbonyl)-L-aspartyl-β-(benzyl ester)-L-prolyl-L-N$^g$-nitro-argininal-semicarbazonyl-4-N-diphenylmethane

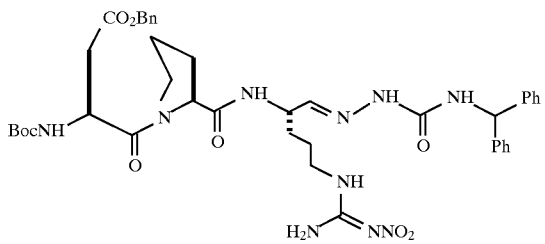
[65]

α-N-(t-butoxycarbonyl)-L-aspartyl-β-(benzyl ester)-L-proline of Example 23 (11.29 g, 26.9 mmole) was dissolved in 60 mL of DMF. This solution was treated with N-methylmorpholine (NMM, 11.9 mL, 108 mmole), BOP (11.9 g, 27 mmole) and the compound of Example 20 (14.64 g, 28 mmole), then allowed to stir for 2 hours. This mixture was poured into 700 mL of ethyl acetate and washed with 1N citric acid, sat'd NaHCO$_3$, water, brine, dried (MgSO$_4$) and concentrated to give a foam. This material was purified by column chromatography (silica gel, 6–20% IPA/DCM) to give 12.5 g (38% overall from the compound of Example 23).

Example 25

Preparation of L-aspartyl-β-(benzyl ester)-L-prolyl-L-N$^g$-nitro-argininal-semicarbazonyl-4-N-diphenylmethane

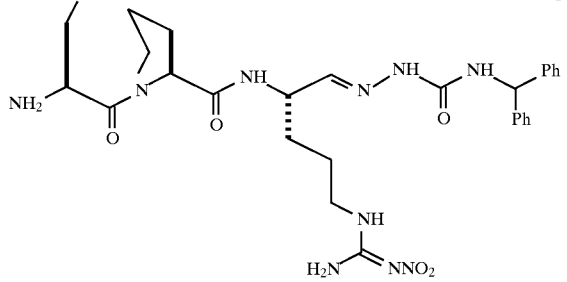
[66]

To a solution of 100 mL of 50% trifluoroacetic acid in dichloromethane which is precooled to 0° C. is added 10.0 g (12.1 mmole) of α-N-(t-butoxycarbonyl)-L-aspartyl-β-(benzyl ester)-L-prolyl-L-N$^g$-nitro-argininal-semicarbazonyl-4-N-diphenylmethane of Example 24. Allow reaction mixture to stir for one-half hour au this temperature, then pour it into 1000 mL of ether to yield a precipitate. Filter off the precipitate and wash with either to give the title compound.

Example 26

Preparation of N-(3-phenylpropionyl)-L-aspartyl-β-(benzyl ester)-L-prolyl-L-N$^g$-nitro-argininal-semicarbazonyl-4-N-diphenylmethane

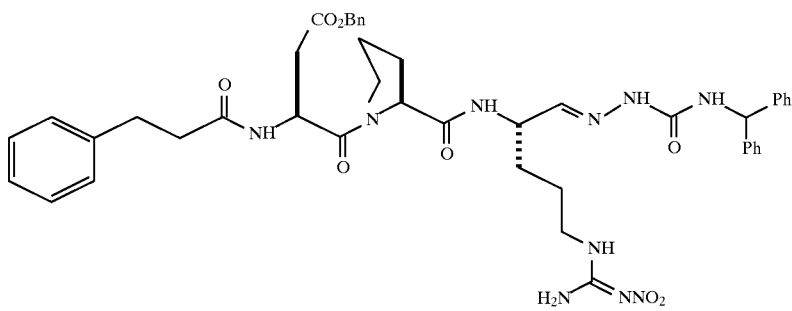
[67]

A solution of 0.91 g (1.08 mmole) of L-aspartyl-β-(benzyl ester)-L-prolyl-L-N$^g$-nitro-argininal-semicarbazonyl-4-N-diphenylmethane of Example 25 in 20 mL of THF. This solution was treated with 0.16 mL dry pyridine and 0.297 mL (2.2 mmole) of 3-phenylpropionic acid chloride, then allowed to stir for one hour with protection from moisture. The reaction mixture was poured into water and extracted with ethyl acetate. The organic extracts were washed successively with 1M aqueous HCl, water, 5% aqueous NaHCO₃, and finally saturated NaCl. The ethyl acetate extract was dried (MgSO₄) and concentrated under reduced pressure. The product was purified by flash chromatography (10% isopropanol in dichloromethane) to give 0.7 g of the title compound, N-(3-phenylpropionyl)-L-aspartyl-β-(benzyl ester)-L-prolyl-L-N$^g$-nitro-argininal-semicarbazonyl-4-N-diphenylmethane.

Example 27

Alternate preparation of N-(3-phenylpropionyl)-L-aspartyl-L-prolyl-L-argininal

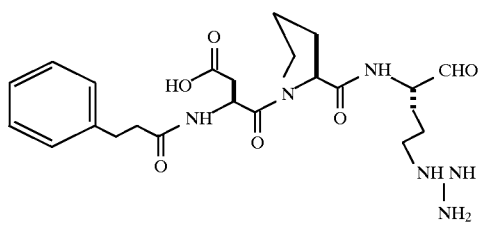

[5]

The compound of the Example 26 was transferred to a teflon HF vessel along with 0.70 mL of anisole. This was cooled to −78° C. under a stream of dry nitrogen. Anhydrous HF (~10 ml) was then condensed into the vessel. The reaction was stirred and allowed to warm to −20° C. and held at that temperature for 30 min. The reaction was allowed to warm to 0° C. and the HF was allowed to evaporate under a stream of dry nitrogen. After the HF had evaporated, 50 ml of 0.1M NH₄HCO₃ was added and the resulting solution was extracted three times with diethyl ether. The aqueous phase (which contained N-(3-phenylpropionyl)-L-aspartyl-L-prolyl-L-argininal-semicarbazone) was then treated with 4.9 mL glacial acetic acid, 5.6 mL 1M aqueous HCl, and 2.7 mL 47% aqueous formaldehyde. This solution was stirred for one hour (to hydrolyse the semicarbazone). The crude reaction mixture was then applied to a 300 mm×50 mm mixed mode column (Alltech, catalog #C-6000B) and eluted with 50 mM phosphate buffer. The fractions containing the title compound were combined and evaporated. The resulting peptide aldehyde was then desalted using reverse phase HPLC on a 10 micron particle size, 300 angstrom pore size C-18 column, eluting with a water-acetonitrile (both containing 0.1% trifluoroacetic acid) gradient, where the gradient ran from 5% to 40% acetonitrile. The column fractions were analyzed by analytical HPLC and fractions containing pure product were pooled and lyophilized to yield the title compound. Fast atom bombardment mass spectrometry confirmed the theoretical molecular weight of 502 a.m.u.

Example 28

Preparation of α-Boc-L-aspartic acid-β-methyl ester

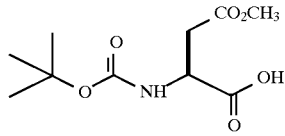

[68]

Dry absolute methanol (100 mL) was treated with sodium metal (0.26 g, 10.8 mmole) under an atmosphere of nitrogen, while stirring in an ice-bath. After the sodium had dissolved, α-Boc-L-aspartic acid-β-benzyl ester (3.2 g, 10.0 mmole) in 20 mL absolute methanol was added. This solution was stirred and the transesterification was followed by TLC. After about 20 hours, 1 mL of glacial acetic acid was added and the reaction was concentrated to a small volume. This residue was poured into 0.5M aqueous HCl and extracted with ethyl acetate. The ethyl acetate phase was washed with water then brine, dried (MgSO₄) and concentrated. The title compound (~3 g) was taken on to the next step.

Example 29

Preparation of α-Boc-L-aspartyl-β-(methyl ester)-L-proline benzyl ester

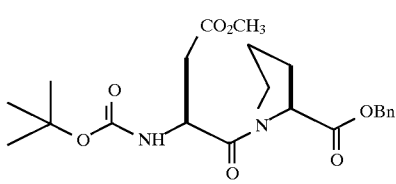

[69]

A solution of compound of Example 28 (α-Boc-L-aspartyl-β-(methyl ester)) (8.9 g, 36 mmole), BOP (15.9 g, 36 mmole), L-proline benzyl ester (8.7 g, 36 mmole) in 90 mL DMF was treated with NMM (19.7 mL). This solution was stirred for 3 hours then poured into 1M HCl and extracted with ethyl acetate. The organic phase was washed successively with 1M HCL, 1M NaOH, water and finally brine, then dried (Na₂SO₄) and concentrated. This gave 16.8 g of crude product. ¹H NMR (CDCl₃) δ1.42 (s, 9H), 2.0 (m, 3H), 2.2 (m, 1H), 2.65 (m, 2H), 3.67 (s, 3H), 3.76 (m, 2H), 4.57 (m, 1H), 4.86 (m, 1H), 5.15 (dd, 2H), 5.40 (d, 1H), 7.35 (m, 5H).

Example 30

Preparation of N-(3-phenylpropionyl)-L-aspartyl-β-(methyl ester)-L-proline benzyl ester

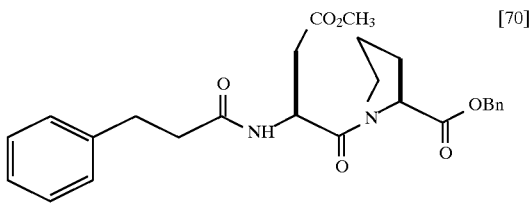

[70]

A solution of the compound of Example 29 (8.4 g, 19.3 mmole) in 100 mL of 75% TFA/CH₂Cl₂ was stirred in an ice bath for 1.5 hours then concentrated to an oil. This residue was dissolved in toluene and concentrated to remove excess TFA. This was dissolved in 75 mL THF, 3-phenylpropionic acid chloride (21.6 mmole) was added followed by 100 mL of aqueous saturated NaHCO₃. This mixture was stirred vigorously for 70 minutes, and then poured into a mixture of ethyl acetate and aqueous saturated NaHCO₃. The mixture was shaken and the organic phase was washed with water and brine, then dried (MgSO₄) and concentrated. The residue was purified by flash chromatography (0–2% CH₃OH/CH₂Cl₂) to give the title compound. TLC (silica); R$_f$=0.5 (2% MeOH/CH₂Cl₂).

Example 31

Preparation of N-(3-phenylpropionyl)-L-aspartyl-β-(methyl ester)-L-proline

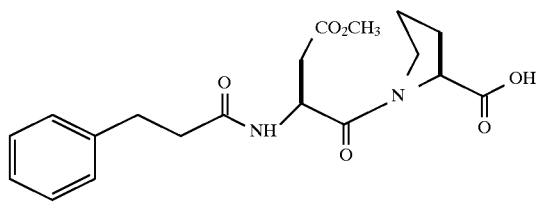

A solution of the compound of Example 30 (2.8 g, 6.0 mmole) in 125 mL of methanol was treated with 280 mg of 10% palladium on carbon and subjected to a hydrogen atmosphere (15 psig) for 1.5 hours with shaking. After this period of time the suspension was filtered and concentrated to give the title compound. $^1$H NMR (CDCl$_3$) δ2.1 (m, 3H), 2.2 (m, 1H), 2.53 (t, 3H), 2.91 (t, 3H), 2.6–2.9 (m, 2H), 3.65 (s, 3H), 3.7 (m, 2H), 4.38 (dd, 1H), 4.86 (m, 1H), 5.05 (m, 2H), 7.23 (m, 5H). 8.37 (d, 1H).

Example 32

Preparation of N-(3-phenylpropionyl)-L-aspartyl-β-(methyl ester)-L-prolyl-N$^g$-nitro-L-argininal semicarbazonyl-4-N-diphenylmethane A solution of the compound of Example 31 (1.7 g, 4.5 mmole), BOP (2.0 g, 4.5 mmole), the compound of Example 20 (2.3 g, 4.5 mmole), in 13 mL of DMF was treated with 2.3 mL NMM. This solution was stirred for 3 hours then poured into water and extracted with ethyl acetate. The organic phase was washed with 1M HCl, 1M NaOH, water then dried(MgSO$_4$) and concentrated. The residue was purified by flash chromatography (0–10% CH$_3$OH/CH$_2$Cl$_2$). The title compound gave a single spot with R$_f$=0.37 (in TLC using 10% methanol in dichloromethane on silica gel).

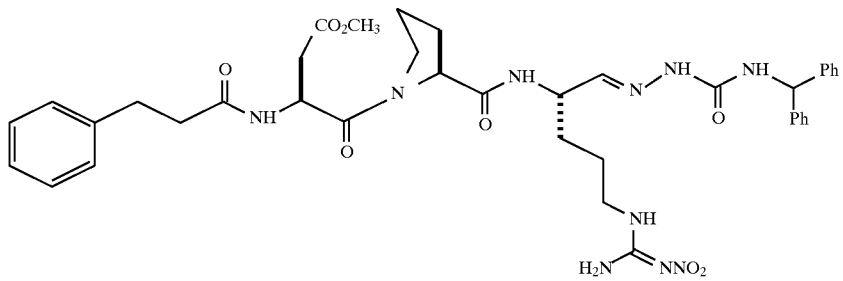

Example 33

Preparation of N-(3-phenylpropionyl)-L-aspartyl-β-(methyl ester)-L-prolyl-L-argininal

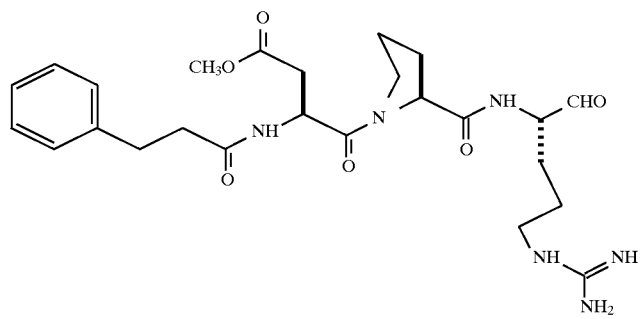

All of the compound of Example 32 was transferred to a teflon HF vessel along with 0.70 mL of anisole. This was cooled to −78° C. under a stream of dry nitrogen. Anhydrous HF (~10 ml) was then condensed into the vessel. The reaction was stirred and allowed to warm to −20° C. and held at that temperature for 30 min. The reaction was allowed to warm to 0° C. and the HF was allowed to evaporate under a stream of dry nitrogen. After the HF had evaporated, 50 ml of 0.1M $NH_4HCO_3$ was added and the resulting solution was extracted three times with diethyl ether. The aqueous phase (which contains N-(3-phenylpropionyl)-L-aspartyl-β-(methyl ester) -L-prolyl-L-argininal-semicarbazone) was then treated with 4.9 mL glacial acetic acid, 5.6 mL 1M aqueous HCl, and 2.7 mL 47% aqueous formaldehyde. This solution was stirred for one hour (to hydrolyse the semicarbazone). The resulting peptide aldehyde is then purified using reverse phase HPLC on a 10 micron particle size, 300 angstrom pore size C-18 column, eluting with a water-acetonitrile (both containing 0.1% trifluoroacetic acid) gradient, where the gradient ran from 5% to 40% acetonitrile. The column fractions were analyzed by analytical HPLC and fractions containing pure product were pooled and lyophilized to yield the title compound. Fast atom bombardment mass spectrometry confirmed the theoretical molecular weight of 516 a.m.u.

Example 34

Preparation of N-(2-propylpentanoyl)-L-aspartyl-β-(methyl ester)-L-proline benzyl ester

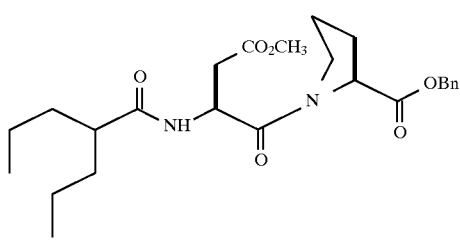

[73]

A solution of the compound of Example 30 (8.4 g, 19.3 mmole) in 100 mL of 75% $TFA/CH_2Cl_2$ was stirred in an ice bath for 1.5 hours then concentrated to an oil. This residue was dissolved in toluene and concentrated to remove excess TFA. This was added to a mixture of 2-propylpentanoic acid (2.44 mL, 15.6 mmole), BOP (6.91 g), and NMM (78 mmole) in 35 mL DMF. This solution was stirred for 1.2 hours and worked up as for Example 33. The product was purified by flash chromatography using a gradient of 10–50% ethyl acetate/hexanes. This gave 2.0 g of the title compound as an oil (TLC $R_f$=0.3 in 40% ethyl acetate/hexanes).

Example 35

Preparation of N-(2-propylpentanoyl)-L-aspartyl-β-(methyl ester)-L-proline

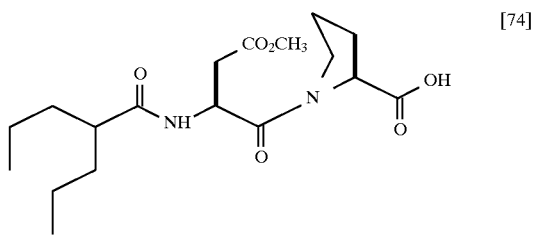

[74]

A solution of the compound of Example 34 (2.0 g, 4.34 mmole) in 90 mL of methanol was treated with 200 mg of 10% palladium on carbon. This was hydrogenated at 15 psig for 1.5 hours. This was filtered and concentrated to give 1.46 g of the title compound. The title compound gave a MP=157°–159° C.

Example 36

Preparation of N-(2-propylpentanoyl)-L-aspartyl-β-(methyl ester)-L-prolyl-N$^g$-nitro-L-argininal semicarbazonyl-4-N-diphenylmethane

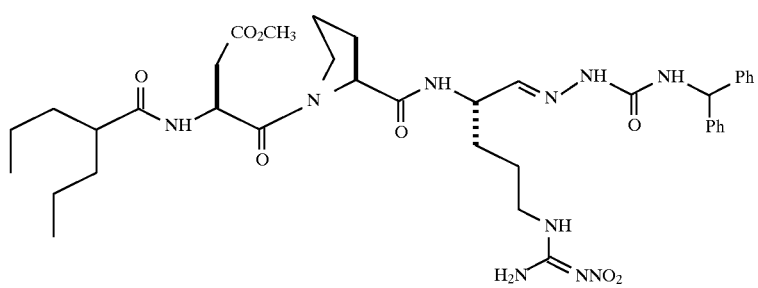

[75]

A solution of the compound of Example 34 (1.67 g, 4.5 mmole), BOP (2.0 g, 4.5 mmole), the compound of Example 20 (2.3 g, 4.5 mmole), in 13 mL of DMF was treated with 2.3 mL NMM. This solution was stirred for 2 hours then poured into water and extracted with ethyl acetate. The organic phase was washed with 1M HCl, 1M NaOH, water then dried ($MgSO_4$) and concentrated. The residue was purified by flash chromatography (0–8% $CH_3OH/CH_2Cl_2$). This gave 1.2 g of pure title compound. The title compound gave a single spot with $R_f$=0.54 (in TLC using 10% methanol in dichloromethane on silica gel).

Example 37

Preparation of N-(2-propylpentanoyl)-L-aspartyl-β-(methyl ester)-L-prolyl-L-argininal

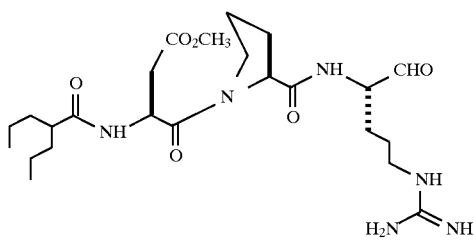
[7]

The compound from Example 36 was deprotected and purified as for example 33 to give title compound. Fast atom bombardment mass spectrometry confirmed the theoretical molecular weight of 510.3 a.m.u.

Example 38

Preparation of N-Boc-D-phenylalanyl-L-aspartyl-L-prolyl-L-argininal

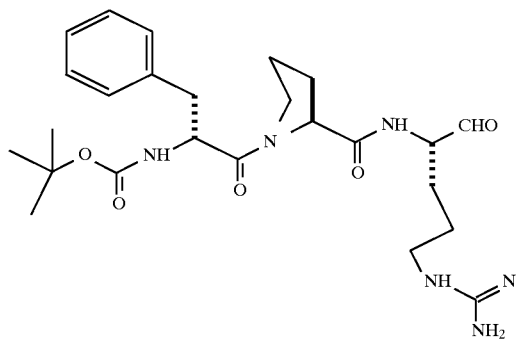

The title compound has been described in the art. See Bajusz, S. et al., Folia Haematol. Leipzig, 109: 16 (1982); Bajusz, S., Symposia Biologica Hungarica, 25: 277 (1984); Bajusz, S. et al., J. Med. Chem., 33: 1729 (1990). It was prepared as described below for use as a control in the assays of Examples A and B.

The title compound was synthesized and purified in a similar manner as described in Example 8. N-Boc-L-proline was first attached to resin of Example 7 followed by N-Boc-D-phenylalanine. The treatment with 50% trifluoroacetic acid was omitted after the last coupling. The title compound was obtained after further deprotection and purification. Fast atom bombardment mass spectrometry confirmed the theoretical molecular weight of 502 a.m.u.

Example 39

Preparation of 3-cyano-2-(1,1-dimethylethoxy) methanamidopropionic acid

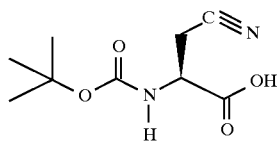
[76]

20.0 g (86 mmol, 1 equiv.) of Boc-L-asparagine was dissolved in 120 mL of dry pyridine and 20.0 g (97 mmol, 1.3 equiv.) of dicyclohexylcarbodiimide dissolved in 60 mL of dry pyridine was added dropwise over a period of 30 minutes. The reaction was stirred for 3 hours at 23° C. and filtered through a 2 μm nylon filter. The filtrate was concentrated in vacuo on a rotary evaporator and 100 mL of water was added. The pH was adjusted to 10 with 40% NaOH (aq.) and the solution filtered through a 2 μm nylon filter once again. The filtrate was passed through a 120 mL bed of Dowex 50X8-400 ion exchange resin and the resin washed with four column volumes of 1:1 methanol:water. The filtrate was concentrated in vacuo to yield 17.5 g (95% yield) of the title compound as a white solid. $^1$H-NMR (CD$_3$OD): 4.40 p.p.m (m, 1H); 2.95 p.p.m. (m, 2H); 1.40 p.p.m. (s, 9H).

Example 40

Preparation of 3-tetrazolyl-2-(1,1-dimethylethoxy) methanamidopropionic acid

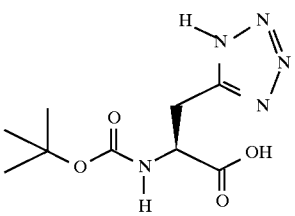
[77]

17.5 g (82 mmol, 1 equiv.) of the compound of Example 39 (3-cyano-2-(1,1-dimethylethoxy)methanamidopropionic acid) was dissolved in 125 mL of THF and 40.5 g (129 mmol, 1.5 equiv.) tributyltin azide was added. The reaction mixture was brought to reflux and held there for 3 days. The reaction mixture was cooled and the volatiles removed in vacuo on the rotary evaporator. The residue was dissolved in 300 mL of 0.5M NaOH and this aqueous solution was washed with ethyl acetate (4×100 mL). The aqueous layer was passed through a 125 mL bed of Dowex 50X8-400 ion exchange resin and the resin washed with four column volumes of 1:1 methanol:water. The volatiles were removed in vacuo on the rotary evaporator to yield 17.9 g of the title compound as a white solid (85% yield). $^1$H-NMR (CD$_3$OD) : 4.55 p.p.m (m, 1H); 3.40 p.p.m. (m, 2H); 1.40 p.p.m. (s, 9H). This material is suitable for use in solid-phase peptide synthesis.

Example 41

Preparation of 3-(N-2-methyl)tetrazolyl-2-(1,1-dimethylethoxy) methanamidopropionic acid, methyl ester and 3-(N-3-methyl)tetrazolyl-2-(1,1-dimethylethoxy) methanamidopropionic acid, methyl ester

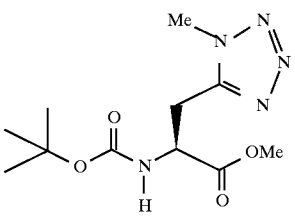
[78]

and

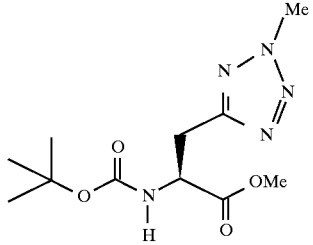

1.5 g (5.8 mmol, 1.0 equiv.) of the compound of Example 40 (3-tetrazolyl-2-(1,1-dimethylethoxy)methanamidopropionic acid) was dissolved in 13 mL of dry DMF and 3.9 g (12.0 mmol, 2.1 equiv.) of cesium carbonate was added. This was followed by the addition of 930 μl (14.5 mmol, 2.5 equiv.) of methyl iodide via syringe. The reaction mixture was stirred at 23° C. for 3 hours and poured into 50 mL of 0.5M HCl. This was extracted with ethyl acetate (3×50 mL). The combined organics were washed with 50 mL 0.5M HCl, 50 mL saturated NaHCO₃, and 50 mL brine. After drying over sodium sulfate, the organics were decanted and the volatiles removed in vacuo on the rotovap to yield a mixture of the title compounds as a yellow oil. The isomers were separated by chromatography on silica (50% EtOAc/hexane) one isomer eluting first (Rf=0.3 vs. Rf=0.15 of the other isomer). Fractions containing pure product were combined and the volatiles removed on the rotary evaporator to yield 0.60 g of pure product for each of the title compounds. ¹H-NMR (CDCl₃): the second eluting isomer gave: 5.8 p.p.m (d, 1H); 4.75 p.p.m (m, 1H); 4.05 p.p.m (s, 3H); 3.75 p.p.m. (s, 3H); 3.4 p.p.m (m, 2H); 1.5 p.p.m. (s, 9H). The first eluting isomer gave 5.75 p.p.m (d, 1H); 4.75 p.p.m (m, 1H); 4.30 p.p.m (s, 3H); 3.75 p.p.m. (s, 3H); 3.65 p.p.m (m, 2H); 1.7 p.p.m. (s, 9H).

Example 42

Preparation of 3-(N-2-methyl)tetrazolyl-2-(1,1-dimethylethoxy)methanamidopropionic acid or 3-(N-3-methyl)tetrazolyl-2-(1,1-dimethylethoxy)methanamidopropionic acid

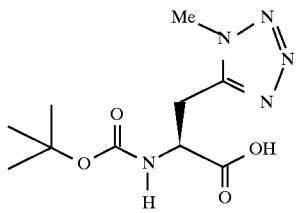

[79]

or

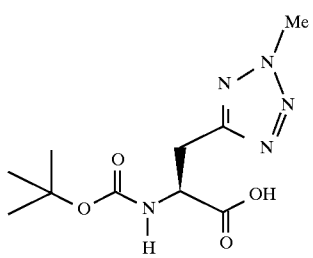

0.5 g (1.75 mmol, 1.0 equiv.) of the compound of Example 41 [3-(N-2-methyl)tetrazolyl-2-(1,1-dimethylethoxy)methanamidopropionic acid, methyl ester or 3-(N-3-methyl)tetrazolyl-2-(1,1-dimethylethoxy)-methamidopropionic acid, methyl ester] is dissolved in 12 mL of methanol and 2.3 mL (1.3 equiv.) of a 1.0M LiOH (aq.) was added. The reaction is stirred for 2 hours at 23° C. when starting material could no longer be seen by TLC analysis (1:1 EtOAc/hexane on silica gel). The reaction mixture is passed through a 10 mL bed of Dowex 50X8-400 ion exchange resin and the resin washed with four column volumes of 1:1 methanol:water. The solvents are removed in vacuo to yield the appropriate title product.

Example 43

Preparation of 3-tetrazolyl-2-(1,1-dimethylethoxy)methanamidopropionic acid, methyl ester

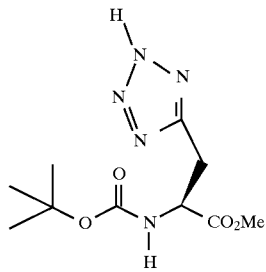

[80]

1.66 g (6.5 mmol, 1 equiv.) of compound of Example 40 (3-tetrazolyl-2-(1,1-dimethylethoxy)-methanamidopropionic acid) was taken up in 26 mL of dry THF and 3.14 g (19.4 mmol, 3 equiv.) of carbonyldiimidazole was added followed by the addition of 88 mg (1.3 mmol, 0.2 equiv.) of imidazole. The reaction mixture was stirred for 3.5 hours at 23° C. 20 mL of methanol was added and the mixture stirred another 0.5 hours. The volatiles were removed in vacuo on the rotary evaporator and the crude product was taken up in 100 mL of ethyl acetate. The organics were washed with 0.5M HCl (2×25 mL) and dried over sodium sulfate. After decanting from the dessicant, the organics were concentrated in vacuo and the title compound was purified by chromatography on a (2–10% MeOH/CH₂Cl₂, 1% acetic acid, silica) to yield 720 mg of product. NMR (CDCl₃) 5.8 ppm (d, 1H), 4.75 ppm (s,1H), 3.8 ppm (s, 3H), 3.55 ppm (m,2H), 1.4 ppm (S, 9H).

Example 44

Preparation of 3-(N-2-benzyloxymethyl)tetrazolyl-2-(1,1-dimethylethoxy)methanamido-propionic acid, methyl ester and 3-(N-3-benzyloxymethyl)tetrazolyl-2-(1,1-dimethylethoxy)methanamidopropionic acid, methyl ester

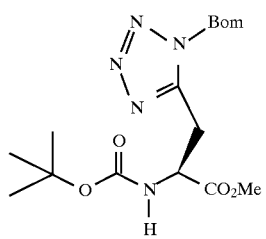

[81]

and

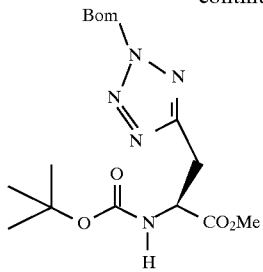

1.28 g (4.7 mmol, 1 equiv.) of compound of Example 43 (3-tetrazolyl-2-(1,1-dimethylethoxy)-methanamidopropionic acid, methyl ester) was taken up in 9.5 mL of dry THF and 0.65 mL (5.6 mmol, 1.2 equiv.) of benzyloxymethyl chloride was added via syringe followed by the addition of 1.05 mL (6.1 mmol, 1.3 equiv.) of diisopropylethylamine. The reaction mixture was stirred for 1 hour at 23° C. and diluted with 100 mL of ethyl acetate. The organics were washed with 0.5M HCl (2×50 mL), saturated NaHCO₃ (50 mL), and brine (50 mL) followed by drying over sodium sulfate. The organics were decanted off and concentrated in vacuo. Chromatography (1:1 EtOAc/hexane, silica) yielded the title compounds (Rf=0.4, 1.05 g; Rf 0.25, 0.67 g). Either isomer may be used in subsequent reactions.

Example 45

3-(N-2-benzyloxymethyl)tetrazolyl-2-(4-methylvaleroylamido) propionic acid, methyl ester or 3-(N-3-benzyloxymethyl)tetrazolyl-2-(4-methylvaleroylamido) propionic acid, methyl ester

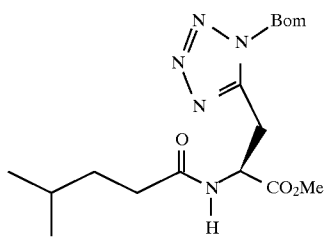

[82]

or

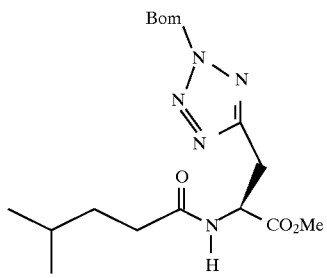

2.0 g of 4-methylvaleric acid is taken up in 10 mL of oxalyl chloride and this mixture is stirred overnight at 23° C. under nitrogen. After this time, 100 mL of dry toluene is added and the volatiles removed in vacuo to yield the acid chloride which is used as indicated below. 1.0 g (2.5 mmol, 1 equiv.) of the compound of Example 44 [3-(N-2-benzyloxymethyl) tetrazolyl-2-(1,1-dimethylethoxy) methanamido-propionic acid, methyl ester or 3-(N-3-benzyloxymethyl)tetrazolyl-2-(1,1-dimethylethoxy) methanamidopropionic acid, methyl ester] is taken up in 10 mL of trifluoroacetic acid at −5° C. and this solution stirred for 0.5 hours followed by concentration in vacuo. The crude trifluoroacetate salt is taken up toluene and this concentrated again to remove any residual trifluoroacetic acid. The crude trifluoroacetate salt is then taken up in 5 mL of dry THF and 0.52 g (3.8 mmol, 1.5 equiv.) of 4-methylvaleroyl chloride, prepared as indicated above, is added followed by the addition of 1.07 mL of triethylamine. The reaction mixture is stirred for 2 hours at 23° C. and diluted with 50 mL of ethyl acetate. The organics are washed with 0.5M HCl (2×25 mL), saturated NaHCO₃ (25 mL), brine (25 mL), and dried over sodium sulfate. After decantation, the organics are concentrated in vacuo and purified by chromatography on silica (1:1 EtOAc/hexane) to yield the corresponding title compound.

Example 46

Preparation of 3-(N-2-benzyloxymethyl)tetrazolyl-2-(4-methylvaleroylamido)propionic acid or 3-(N-3-benzyloxymethyl)tetrazolyl-2-(4-methylvaleroylamido)propionic acid

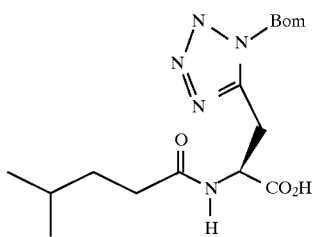

[83]

or

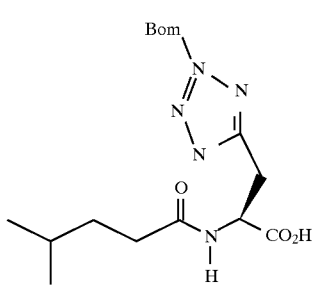

A 0.15M solution of the compound of Example 45 [3-(N-2-benzyloxymethyl)tetrazolyl-2-(4-methylvaleroylamido)propionic acid, methyl ester or 3-(N-3-benzyloxymethyl)tetrazolyl-2-(4-methylvaleroylamido) propionic acid, methyl ester] in methanol is prepared and 1.5 equivalents of a 1M LiOH (aq.) is added. The reaction mixture is stirred until no starting material remains by TLC (about 3 hours) and passed through Dowex 50X8-400 ion exchange resin and the resin washed with four column volumes of 1:1 methanol:water. The filtrate concentrated in vacuo to wield the corresponding title compound.

Example 47
Preparation of Boc-L-prolyl-L-N<sup>g</sup>-nitro-argininal-semicarbazonyl-4-N-diphenylmethane

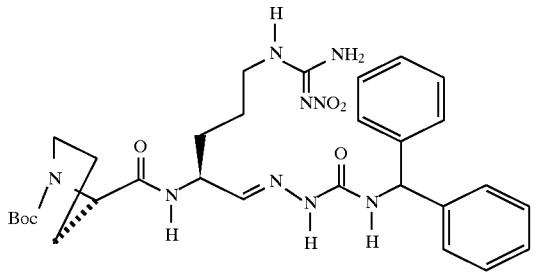

[84]

5.0 g (9.6 mmol, 1 equiv.) of the compound of Example 20 (N<sup>g</sup>-nitro-arginal-semicarbazonyl-4-N-diphenylmethane trifluoroacetate salt), 2.15 g (11.5 mmol, 1.2 equiv.) of N-t-butoxycarbonyl-L-proline, 5.53 g (12.5 mmol, 1.3 equiv.) of BOP reagent, and 0.15 g (0.96 mmol, 0.1 equiv.) of N-hydroxybenztriazole monohydrate are taken up in 38 mL of dry DMF and 6.3 mL (57.6 mmol, 6 equiv.) of N-methylmorpholine is added via syringe. The reaction mixture is stirred for 3 hours and diluted with 300 mL of ethyl acetate. The organics are washed with 4M HCl (30 mL), 1M NaOH (2×30 mL), and brine (30 mL) followed by drying over sodium sulfate. The organics are decanted and concentrated in vacuo to yield crude title compound which can be chromatographed with 1:10 MeOH/methylene chloride on silica.

Example 48
Preparation of 3-(N-2-benzyloxymethyl)tetrazolyl-2-(4-methylvaleroylamido)propionoyl-L-prolyl-L-N<sup>g</sup>-nitro-argininal-semicarbazonyl-4-N-diphenylmethane or 3-(N-3-benzyloxymethyl) tetrazolyl-2-(4-methylvaleroylamido) propionoyl-L-prolyl-L-N<sup>g</sup>-nitro-argininal-semicarbazonyl-4-N-diphenylmethane

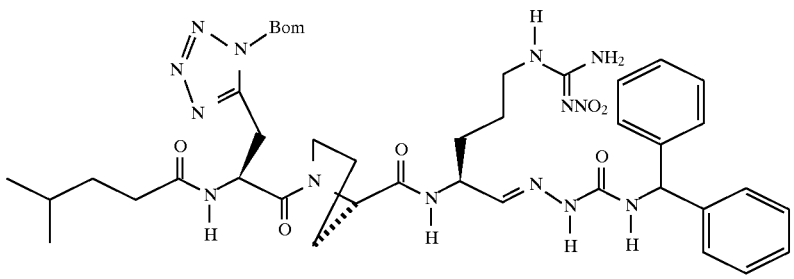

[85]

or

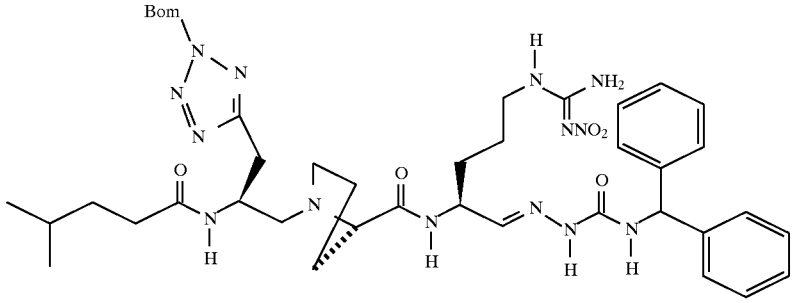

2.5 mmol (1 equiv.) of the compound of Example 47 (Boc-L-prolyl-L-N<sup>g</sup>-nitro-argininal-semicarbazonyl-4-N-diphenylmethane) is taken up in 10 mL of trifluoroacetic acid at −5° C. and this solution stirred for 0.5 hours followed by concentration in vacuo. The crude trifluoroacetate salt is taken up toluene and this concentrated again to remove any residual trifluoroacetic acid. 3 mmol (1.2 equiv.) of the compound of Example 46 [3-(N-2-benzyloxymethyl) tetrazolyl-2-(4-methylvaleroylamido) propionic acid or 3-(N-3-benzyloxymethyl) tetrazolyl-2-(4-methylvaleroylamido) propionic acid], 3.25 mmol (1.3 equiv.) of BOP reagent, and 0.25 mmol (0.1 equiv.) of N-hydroxybenzotriazole monohydrate are taken up in 10 mL of dry DMF and 15 mmol (6 equiv.) of N-methylmorpholine is added via syringe. The reaction mixture is stirred for 3 hours and diluted with 100 mL of ethyl acetate. The organics are washed with 4M HCl (10 mL), 1M NaOH (2×10 mL), and brine (10 mL) followed by drying over sodium sulfate. The organics are decanted and concentrated in vacuo to yield crude product which can be chromatographed with 1:10 MeOH/methylene chloride on silica to yield the corresponding title compound.

Example 49

Preparation of 3-tetrazolyl-2-(4-methylvaleroylamido) propionoyl-L-prolyl-L-argininal

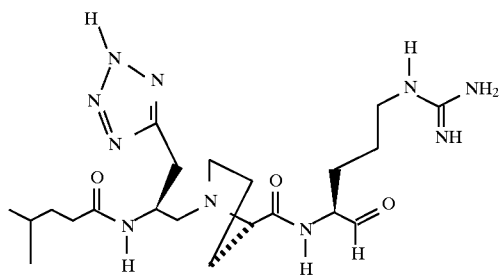
[11]

All of product of Example 48 is transferred to a teflon HF vessel along with 0.70 mL of anisole. This is cooled to −78° C. under a stream of dry nitrogen. Anhydrous HF (~10 ml) is then condensed into the vessel. The reaction is stirred and allowed to warm to −20° C. and held at that temperature for 30 minutes. The reaction is allowed to warm to 0° C. and the HF is allowed to evaporate under a stream of dry nitrogen. After the HF is evaporated, 50 ml of 0.1M $NH_4HCO_3$ is added and the resulting solution is extracted three times with diethyl ether. The aqueous phase (which contains 2-(4-methylvaleroylamido)propionoyl-L-prolyl-L-argininal semicarbazone) is then treated with 4.9 mL glacial acetic acid, 5.6 mL 1M aqueous HCl, and 2.7 mL 479, aqueous formaldehyde. This solution is stirred for one hour (to hydrolyze the semicarbazone). The resulting peptide aldehyde is then purified using reverse phase HPLC on a 10 micron particle size, 300 angstrom pore size C-18 column, eluting with a water-acetonitrile (both containing 0.1% trifluoroacetic acid) gradient, where the gradient is run from 5% to 40% acetonitrile. The column fractions are analyzed by analytical HPLC and fractions containing pure product are pooled and lyophilized to yield the title product.

Alternatively, the compound of Example 49 may be synthesized by the route shown in Examples 50 through 56.

Example 50

Preparation of 1-amido-3-benzyloxymethanamido-1,4-butanedioic acid, methyl ester

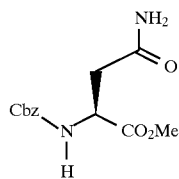
[86]

15.0 g (56.4 mmol, 1 equiv.) of Cbz-L-asparagine was dissolved in 100 mL of dry methylene chloride and 50 mL (573 mmol, 10 equiv.) of oxalyl chloride was added dropwise over a period of 10 minutes. The reaction was stirred for 4 hours at 23° C. followed by removing the volatiles in vacuo on a rotary evaporator. 100 mL of methanol was added and the mixture was stirred for 0.5 hours at 23° C. The reaction mixture was concentrated in vacuo and the crude product purified by flash chromatography (0–5% methanol/methylene chloride) to yield 12.45 g of title compound. $^1$H-NMR (CDCl3): 7.4 p.p.m (m, 5H); 6.1 p.p.m. (d, 1H); 5.8 p.p.m. (d, 2H); 5.1 p.p.m. (s, 2H); 4.6 p.p.m. (m, 1H); 3.75 p.p.m. (s, 3H); 2.85 p.p.m. (m, 2H)

Example 51

Preparation of 3-cyano-2-benzyloxymethanamido propionic acid, methyl ester

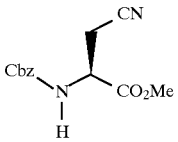
[87]

5.0 g (17.9 mmol, 1 equiv.) of the compound of Example 50 (Cbz-L-asparagine, methyl ester) was dissolved in 10 mL of dry pyridine and 3.0 mL (23.2 mmol, 1.3 equiv.) of benzene sulfonyl chloride was added via syringe. The reaction was stirred for 3 hours at 50° C. 50 mL of 1M HCl was added and the aqueous solution was extracted with ethyl acetate (2×100 mL). The organics were combined and washed with 50 mL of 1M HCl, 50 mL of saturated $NaHCO_3$, and brine. After drying over sodium sulfate, the organics were decanted and concentrated in vacuo. The crude product was purified by flash chromatography (10% EtOAc/methylene chloride, Rf=0.45) to yield 4.1 g of the title compound. $^1$H-NMR (CDCl$_3$): 7.4 p.p.m (m, 5H); 5.7 p.p.m. (m, 1H); 5.1 p.p.m. (s, 2H); 4.6 p.p.m. (m, 1H); 3.8 p.p.m. (s, 3H); 3.0 p.p.m. (m, 2H).

Example 52

Preparation of 3-tetrazolyl-2-benzyloxymethanamido propionic acid, methyl ester

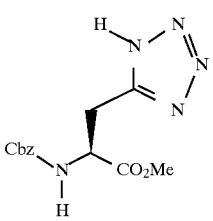
[88]

2.5 g (9.54 mmol, 1 equiv.) of the compound of Example 51 (3-cyano-2-benzyloxymethanamidopropionic acid, methyl ester) was dissolved in 10 mL of dry THF and 3.0 g (9.54 mmol, 1 equiv.) of tri-n-butyltin azide was added. The reaction was refluxed for 72 hours followed by concentration in vacuo. 50 mL of 1M NaOH was added and the aqueous solution was extracted with ethyl acetate (3×50 mL). The aqueous solution was acidified to pH=1 with 4M HCl and extracted with ethyl acetate (4×60 mL). After drying over sodium sulfate, the organics were decanted and concentrated an vacuo to yield 2.5 g of the title compound. $^1$H-NMR (CDCl$_3$): 7.3 p.p.m (m, 5H); 6.1 p.p.m. (m, 1H); 5.1 p.p.m. (s, 2H); 4.8 p.p.m. (m, 1H); 3.8 p.p.m. (s, 3H); 3.5 p.p.m. (m, 2H).

Example 53

Preparation of 3-tetrazolyl-2-amino propionic acid, methyl ester hydrochloride

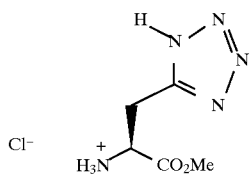

[89]

0.53 g (1.74 mmol, 1 equiv.) of the compound of Example 52 (3-tetrazolyl-2-benzyloxymethanamidopropionic acid, methyl ester) was dissolved in 30 mL of methanol and 1 mL of conc. HCl was added. The reaction was flushed with nitrogen and 80 mg of 10% palladium on carbon was added. The solution was hydrogenated for 2 hours at 40 psi. Filtration of the catalyst followed by concentration in vacuo yielded 354 mg of the title compound. $^1$H-NMR (CD$_3$OD): 4.7 p.p.m. (m, 1H); 3.8 p.p.m. (s, 3H); 3.6 p.p.m. (m, 2H).

Example 54

Preparation of 3-tetrazolyl-2-(4-methylvaleroylamido) propionic acid, methyl ester

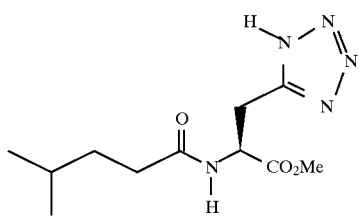

[90]

353 mg (1.74 mmol, 1 equiv.) of the compound of Example 53 (3-tetrazolyl-2-aminopropionic acid, methyl ester hydrochloride), 262 µL (2.09 mmol, 1.2 equiv.) of 4-methylvaleric acid, 1.0 g (2.26 mmol, 1.3 equiv.) of BOP reagent, and 27 mg (0.174 mmol, 0.1 equiv.) of N-hydroxybenztriazole monohydrate were taken up in 5 mL of dry DMF and 960 µL (8.7 mmol, 5 equiv.) of N-methylmorpholine was added via syringe. The reaction mixture was stirred for 18 hours at 23° C. followed by dilution with 100 mL of ethyl acetate. The organics are washed with 20% citric acid (10 mL) and brine (10 mL) followed by drying over sodium sulfate. The organics are decanted and concentrated in vacuo to yield crude product which was chromatographed with MeOH/methylene chloride (2–10% 1% acetic acid) on silica to yield 230 mg of the title compound (Rf=0.30; 10% MeOH/methylene chloride, 1% acetic acid). $^1$H-NMR (CDCl$_3$): 7.0 p.p.m. (d, 1H); 5.05 p.p.m. (m, 1H); 3.8 p.p.m. (s, 3H); 3.6 p.p.m. (m, 2H), 1.5 p.p.m. (m, 3H); 0.8 p.p.m. (d, 6H).

Example 55

Preparation of 3-tetrazolyl-2-(4-methylvaleroylamido) propionic acid

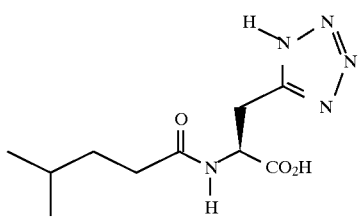

[91]

51 mg (0.19 mmol, 1 equiv.) of the compound of Example 54 (3-tetrazolyl-2-(4-methylvaleroylamido)propionic acid, methyl ester), 16 mg (0.38 mmol, 2 equiv.) of lithium hydroxide were taken up in 1.5 mL of water and the reaction mixture was stirred for 2 hours. 35 µL of 1M HCl was added and the solution concentrated in vacuo to yield the title compound, which was used in the subsequent reaction as is. $^1$H-NMR (CD$_3$OD): 4.6 p.p.m. (m, 1H); 3.4 p.p.m. (m, 1H); 3.2 p.p.m. (m, 1H); 2.15 p.p.m. (m, 2H); 1.4 p.p.m. (m, 3H); 0.8 p.p.m. (d, 6H).

Example 56

Preparation of 3-(N-3-benzyloxymethyl)tetrazolyl-2-(4-methylvaleroylamido)propionyl-L-prolyl-L-N$^g$-nitro-argininal-semicarbazonyl-4-N-diphenylmethane

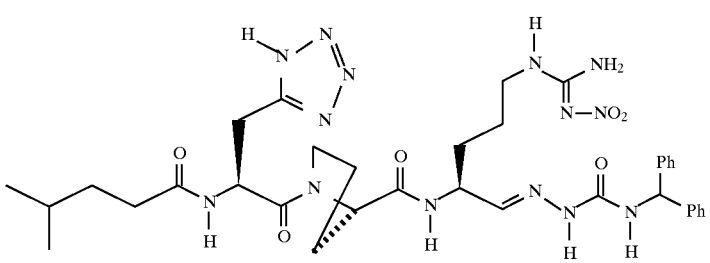

[92]

120 mg (0.28 mmol, 1 equiv.) of the compound of Example 19 (Boc-L-prolyl-L-N$^g$-nitro-argininal-semicarbazonyl-4-N-diphenylmethane) was taken up in 5 mL of trifluoroacetic acid at −5° C. and this solution stirred for 0.5 hours followed by concentration in vacuo. The crude trifluoroacetate salt is taken up toluene and this concentrated again to remove any residual trifluoroacetic acid. 48 mg (0.23 mmol, 1.2 equiv.) of the compound of Example 55 (3-tetrazolyl-2-(4-methylvaleroylamido)propionic acid), 48 mg (0.25 mmol, 1.3 equiv.) of 1-(3-dimethylaminopropyl)-3-ethylcarbodiimide hydrochloride, and 2 mg (0.02 mmol, 0.1 equiv.) of 4-dimethylaminopyridine was taken up in 3 mL of dry DMF and 100 μL (0.57 mmol, 3 equiv.) of diisopropylethylamine was added via syringe. The reaction mixture was stirred for 18 hours at 23° C. and poured into 10 mL of 20% citric acid. The aqueous solution was extracted with ethyl acetate (6×15 mL) and the combined organics dried over sodium sulfate. The organics were decanted and concentrated in vacuo to yield crude product which was chromatographed on a 2 mm preparative TLC silica gel plate (10% MeOH/methylene chloride, 1% acetic acid). The band with an Rf of 0.25 was removed, taken up in 10% methanol/ethyl acetate, and filtered. Removal of the volatiles in vacuo yielded 30 mg of the title compound. $^1$H-NMR (CD$_3$OD): 7.3 p.p.m. (m, 10H); 7.1 p.p.m. (d, 1H); 6.1 p.p.m. (s, 1H); 4.7 p.p.m. (m, 1H); 4.5 p.p.m. (m, 1H); 4.3 p.p.m. (m, 1H); 3.6 p.p.m. (m, 1H); 3.2 p.p.m. (m, 2H); 2.8 p.p.m. (m, 1H); 2.1 p.p.m. (m, 3H); 1.2–1.9 p.p.m. (m, 13H).

Example 57

Preparation of 3-tetrazolyl-2-(4-methylvaleroylamido) propionyl-L-prolyl-L-argininal

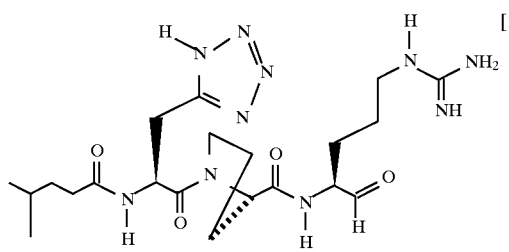

[11]

All of product of Example 56 was transferred to a teflon HF vessel along with 0.70 mL of anisole. This was cooled to −78° C. under a stream of dry nitrogen. Anhydrous HF (~10 ml) was then condensed into the vessel. The reaction was stirred and allowed to warm to −20° C. and held at that temperature for 30 minutes. The reaction was allowed to warm to 0° C. and the HF was allowed to evaporate under a stream of dry nitrogen. After the HF was evaporated, 50 ml of 0.1M NH$_4$HCO$_3$ was added and the resulting solution was extracted three times with diethyl ether. The aqueous phase (which contained 2-(valeroylamido) propionyl-L-prolyl-L-argininal-semicarbazone) was then treated with 4.9 mL glacial acetic acid, 5.6 mL 1M aqueous HCl, and 2.7 mL 47% aqueous formaldehyde. This solution was stirred for one hour (to hydrolyse the semicarbazone). The resulting peptide aldehyde was then purified using reverse phase HPLC on a 10 micron particle size, 300 angstrom pore size C-18 column, eluting with a water-acetonitrile (both containing 0.1% trifluoroacetic acid) gradient, where the gradient was run from 5% to 40% acetonitrile. The column fractions were analyzed by analytical HPLC and fractions containing pure product were pooled and lyophilized to yield the title product. Fast atom bombardment mass spectrometry confirmed the theoretical molecular weight of 492 a.m.u.

Example 58

Preparation of N-Boc-L-aspartyl-(β-methyl ester)-L-proline-O-benzyl ester

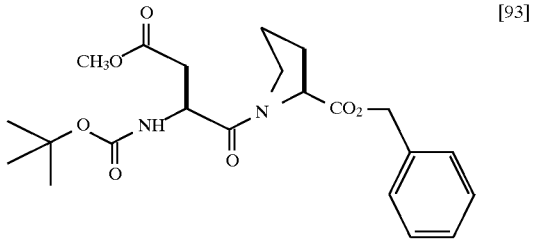

[93]

A solution of 57.58 g (0.232 moles) of N-Boc-L-aspartic acid-(β-methyl ester), 50 g (0.208 moles) of L-proline-(O-benzyl ester) hydrochloride, 640 ml of dry dimethylformamide (DMF) and 102 g (0.237 moles) of BOP, was treated with 127.47 mL of 4-methylmorpholine (NMM) and stirred overnight under nitrogen. This solution was poured into 1000 mL of water and extracted three times with 300 mL of ethyl acetate. The combined organic phase was washed three times with 300 mL of water, 10% HCl, saturated sodium bicarbonate solution, and brine. The organic phase was dried over magnesium sulfate and evaporated under reduced pressure. This gave 91.39 g (97.7 % yield) (viscous oil) of the title compound. $^1$H NMR (CDCl$_3$): 7.33 (M, 5H), 5.42 (m, 1H), 5.19, 5.12 (d, d, 2H), 4.56 (b, 1H),3.77 (m, 2H), 3.67 (s, 3H) , 2.72 (m, 1H), 2.58 (m, 1H), 2.18 (m, 1H), 1.97 (m, 1H), 1.43 (s, 9H).

Example 59

Preparation of L-aspartyl-β-(methyl ester)-L-proline-O-benzyl ester hydrochloride salt

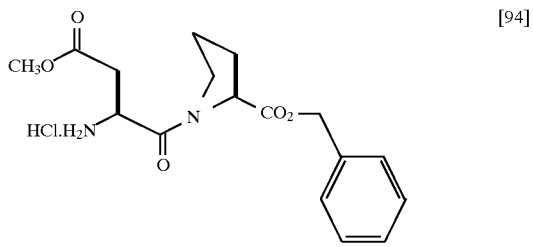

[94]

A solution of 125.2 g (0.288 moles) of compound of Example 58 was dissolved in 500 mL of dioxane and added to a solution of 500 mL of dioxane saturated with HCl (g) at 0° C. After 3.5 hours, the TLC showed no starting material remained. The solvent was evaporated under vacuum to yield a brown glass. The solid remained under vacuum for 24 hours and gave 145 g (>100 % yield) of crude title compound, which was used without further purification.

Example 60

Preparation of N-(butylsulfonyl)-L-aspartyl-(β-methyl ester)-L-proline-O-benzyl ester

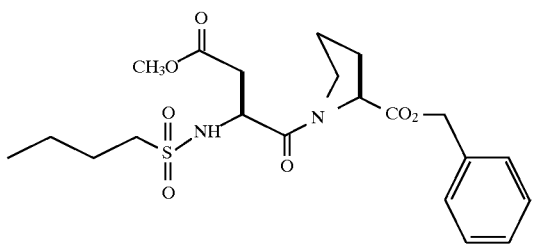
[95]

A solution of 12.2 g (0.033 moles) of compound of Example 59, 3.9 mL (0.03 moles) of n-butyl-sulfonyl chloride, 500 ml of acetonitrile and 7 mL of dry DMF was cooled to 0° C. This solution was treated with 7 mL of pyridine and allowed to warm to room temperature overnight. This solution was poured into 1000 mL of water and extracted three times with 300 mL of ethyl acetate. The combined organic phase was washed three times with 300 mL of water, 10%, HCl, saturated sodium bicarbonate solution, and brine. The organic phase was dried over magnesium sulfate and evaporated under reduced pressure. This gave a brown oil, 5.35 g (36.3 % yield), of the title compound. Rf=0.95 (10% MeOH/methylene chloride).

Example 61

Preparation of N-(butylsulfonyl)-L-aspartyl-(β-methyl ester)-L-proline

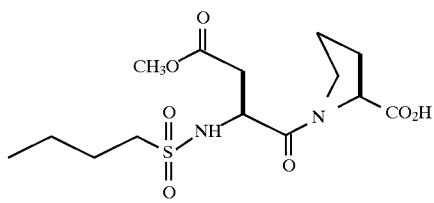
[96]

A solution of 5.35 g (0.012 moles) of compound of Example 60, 250 mL of methanol and 1.3 g of palladium 10% on carbon, was pressurized with 40 psi of hydrogen in a Parr Hydrogenator. This mixture was shaken for two hours and then the mixture was filtered through celite using a fine fritted filter. The solution was concentrated to a white glass, 3.33 g (77.6%), of the title compound. Rf=0.18 (10% MeOH/methylene chloride).

Example 62

Preparation of N-(butylsulfonyl)-L-aspartyl-(β-methyl ester)-L-prolyl-L-argininal

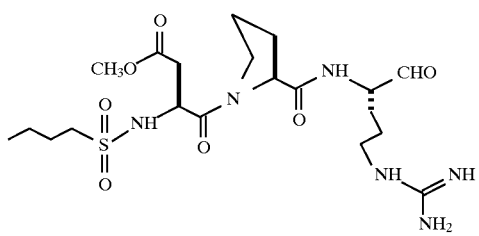
[26]

0.5 g (0.25 mmole protected amino groups) of the resin from Example 7 was placed in a reaction vessel, then was washed three times with 5–10 mL of dichloromethane. The resin was made ready for use by removing the Boc protecting groups by successive treatment with two 5–10 mL portions of 50% trifluoroacetic acid (in dichloromethane) for a total time of 35 minutes. After neutralizing the acidity by soaking the resin in 5–10 mL of 5% diisopropylethylamine (in dimethylformamide) for 7 minutes, the resin was successively washed with two 5–10 mL portions each of dimethylformamide, dichloromethane and dimethylformamide.

The deblocked resin was suspended in 5 mL of dimethylformamide, then was treated with NMM (101 mg, 1.0 mmole), the compound of Example 61 (397 mg, 1.0 mmole), TBTU (321 mg, 1.0 mmole), HOBt (135 mg, 0.9 mmole), and DMF (3 mL). After three hours of agitation at room temperature (20°–25° C.), the resin was filtered off, washed with three 5–10 mL portions of dimethylformamide, dichloromethane, methanol and diethyl ether, and then was dried under vacuum.

The dried resin was placed in a reaction vessel and anisole (0.5 mL) was added. After cooling the reaction vessel to −20° C., gaseous hydrofluoric acid (12.0 mL) was distilled to the reaction mixture with stirring. After stirring for 2 hours at −20° C., the reaction mixture was allowed to warm to 0° C., the hydrofluoric acid was then distilled off with a stream of $N_2$ at 0° C. The resin was washed with two 5–10 mL portions of diethyl ether, then the title compound was extracted from the resin with 0.1M ammonium bicarbonate (50 mL) and water (200 mL). The aqueous extracts were combined, extracted with three 5–10 mL portions of diethyl ether, frozen and lyophilized to give crude semicarbazone of title product (170 mg).

The crude semicarbazone (40 mg, 0.06 mmole) was placed in a reaction vessel, followed by 1.4 mL acetic acid, 2.9 mL THF and 1.4 mL of trifluoroacetic acid (in water) at pH 1. Stirring of the reaction mixture was commenced and 0.2 mL of ethyl acetoacetate was added. Additional 0.2 mL portions of ethyl acetoacetate were added every 1–8 hours until the semicarbazone was converted to the crude title product. The reaction mixture was then reduced to dryness in vacuo.

The crude title product was purified using reverse phase HPLC on a 10 micron particle size, 300 angstrom pore size C-18 column, eluting with a water-acetonitrile (both containing 0.1% trifluoroacetic acid) gradient, where the gradient ran from 5% to 40% acetonitrile. The column fractions were analyzed by analytical HPLC and fractions containing pure product were pooled and lyophilized to yield pure title product. Fast atom bombardment mass spectrometry confirmed the theoretical molecular weight of 504 a.m.u.

Example 63

Preparation of N-(2-naphthylsulfonyl)-L-aspartyl-(β-methyl ester)-L-proline-O-benzyl ester

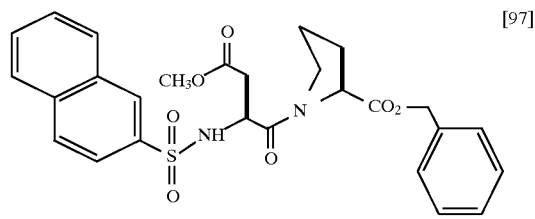
[97]

A solution of 12.2 g (0.033 moles) of compound of Example 59, 6.8 g (0.03 moles) of 2-naphthalene-sulfonyl chloride, 500 mL of acetonitrile and 7 mL of dry DMF was cooled to 0° C. This solution was treated with 7 mL of pyridine and allowed to warm to room temperature overnight. This solution was poured into 1000 mL of water and extracted three times with 300 mL of ethyl acetate. The combines organic phase was washed three times with 300 mL of water, 10% HCl, saturated sodium bicarbonate solution, and brine. The organic phase was dried over magnesium sulfate and evaporated under reduced pressure. This gave a light yellow solid, 12.76 g (81.2% yield), of the title compound. Rf=0.72 (10% MeOH/methylene chloride).

Example 64

Preparation of N-(2-naphthylsulfonyl)-L-aspartyl-(β-methyl ester)-L-proline

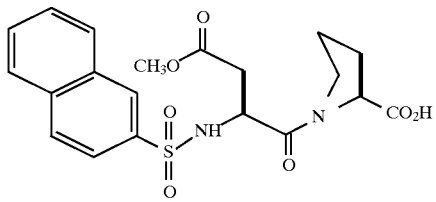

[98]

A solution of 12.76 g (0.024 moles) of the compound of Example 63, 250 mL of methanol and 1.3 g of 10% palladium on carbon, was pressurized with 40 psi of hydrogen in a Parr Hydrogenator. This mixture was shaken for two hours and then the mixture was filtered thru celite through a fine fritted filter. The solution was concentrated to a white solid, 9.22 g (87.3%), of the title compound. Rf=0.12 (10% MeOH/methylene chloride).

Example 65

Preparation of N-(2-naphthylsulfonyl)-L-aspartyl-(β-methyl ester)-L-prolyl-L-argininal

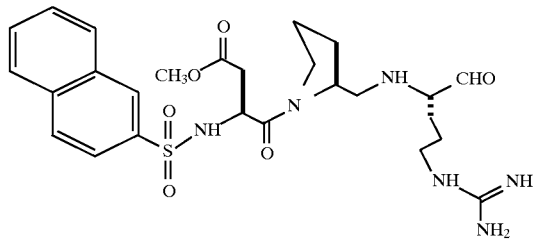

[28]

The title compound was made in the same manner as described in Example 62 substituting the compound of Example 64 (397 mg, 1.0 mmole) for the compound of Example 61. Fast atom bombardment mass spectrometry confirmed the theoretical molecular weight of 574 a.m.u.

Example 66

Preparation of N-(4-methylphenylsulfonyl)-L-aspartyl-(β-methyl ester)-L-proline-O-benzyl ester

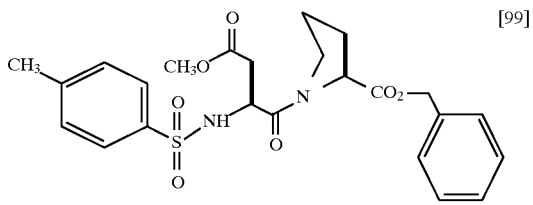

[99]

A solution of 12.2 g (0.033 moles) of compound of Example 59, 5.72 (0.03 moles) of tosyl chloride, 450 mL of acetonitrile and 7 mL of dry DMF was cooled to 0° C. This solution was treated with 7 mL of pyridine and allowed to warm to room temperature overnight. This solution was poured into 1000 mL of water and extracted three times with 300 mL of ethyl acetate. The combines organic phase was washed three times with 300 mL of water, 10% HCl, saturated sodium bicarbonate solution, and brine. The organic phase was dried over magnesium sulfate and evaporated under reduced pressure. This gave a light brown oil, 4.21 g (28.7 yield), of the title compound. Rf=0.90 (10% MeOH/methylene chloride).

Example 67

Preparation of N-(4-methylphenylsulfonyl)-L-aspartyl-(β-methyl ester)-L-proline

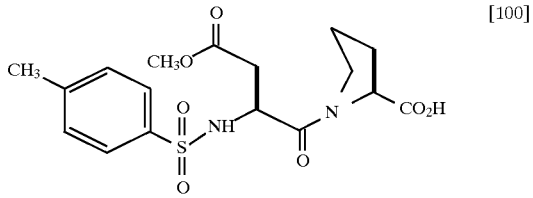

[100]

A solution of 4.21 g (0.012 moles) of the compound of Example 66, 250 mL of methanol and 1.3 g of 10% palladium on carbon, was pressurized with 40 psi of hydrogen in a Parr Hydrogenator. This mixture was shaken for two hours and then the mixture was filtered through celite using a fine fritted filter. The solution was concentrated to a white glass, 3.17 g (92.4%), of the title compound. Rf=0.11 (10% MeOH/methylene chloride).

Example 68

Preparation of N-(4-methylphenylsulfonyl)-L-aspartyl-(β-methyl ester)-L-prolyl-L-argininal

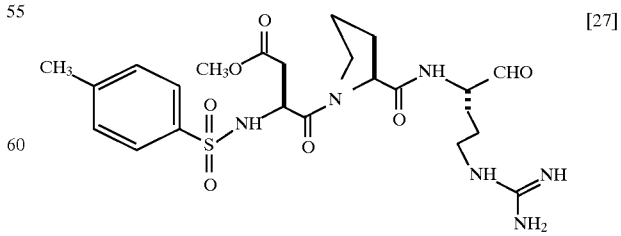

[27]

The title compound was made in the same manner as described in Example 62 substituting the compound of Example 67 (397 mg, 1.0 mmole) for the compound of Example 61. Fast atom bombardment mass spectrometry confirmed the theoretical molecular weight of 538 a.m.u.

Example 69

Preparation of N-Boc-L-aspartic acid-(β-methyl ester)-O-benzyl ester

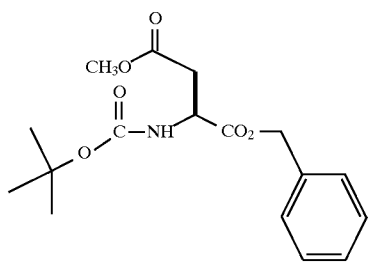

[101]

To a solution 6.2 g (25 mmole) of N-Boc-aspartic acid-(β-methyl ester) in dry acetonitrile (60 mL) cooled to 0° C. was added, HOBt (5.1 g, 33 mmole) followed by EDC (5.3 g, 27.5 mmole) and benzyl alcohol (2.58 mL, 25 mmole). The mixture was then stirred for 12 hours in the ice bath which eventually warmed to room temperature. The crude reaction mixture was reduced in vacuo, and then ethyl acetate (200 mL) was added, followed by water (50 mL). The organic phase was then separated and washed with saturated sodium bicarbonate solution (50 mL), brine (50 mL), and a saturated citric acid solution (50 mL). The organic phase was separated and dried over magnesium sulfate. The solution was then filtered and then the volume was reduced in vacuo to provide crude ester. The product was purified by flash column chromatography (SiO₂, 100 g) using 4:1 (hexanes:ethyl acetate) eluent to provide 3.5 g (41% yield) of a white solid of the title compound. Rf=0.32 (4:1 hexanes:ethyl acetate).

Example 70

Preparation of L-aspartic acid-(β-methyl ester)-O-benzyl ester hydrochloride salt

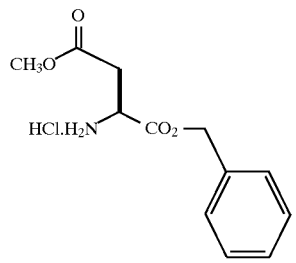

[102]

To a solution of the compound of Example 69 (3.5 g, 10.3 mmole) in 50 mL dry dioxane at 0° C. was added 50 mL of a 4M solution of HCl in dioxane. The mixture was stirred for 1 hour at 0° C. until TLC (4:1 hexanes:ethyl acetate) indicated disappearance of starting material. The solution was then reduced in vacuo to provide 2.65 g (94 yield) of the title compound as white solid. Rf=0.2 ((4:1 hexanes:ethyl acetate).

Example 71

Preparation of N-benzylsulfonyl-L-aspartic acid-(β-methyl ester)-O-benzyl ester

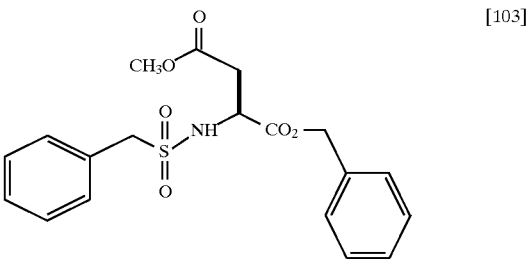

[103]

To a solution of the compound of Example 70 (2.6 g, 9.5 mmole) in dry acetonitrile (50 mL) at 0° C. was added, the benzyl sulfonyl chloride (1.8 g, 9.5 mmole) followed by pyridine (2.4 mL, 30.0 mmole). The mixture was allowed to warm to room temperature overnight (12 hours). The mixture was then reduced in vacuo and then ethyl acetate (150 mL) was added. The organic phase was then washed with saturated sodium bicarbonate (50 mL), brine (50 mL) and saturated citric acid (50 mL). The organic phase was dried (magnesium sulfate), filtered and reduced in vacuo to provide crude material. The compound was purified by flash chromatography (SiO₂, 100 g) using 7:3 hexanes:ethyl acetate as eluent to provide 2.87 g (78% yield) of the title compound as an oil. Rf=0.39 (1:1 hexanes:ethyl acetate)

Example 71

Preparation of N-benzylsulfonyl-L-aspartic acid-(β-methyl ester)

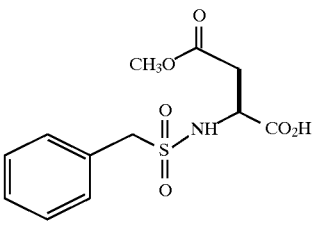

[104]

To a solution of the compound of Example 70 (2.8 g, 7.3 mmole) in methanol (60 mL) was added, 0.5 g 10% Pd/C and the mixture was hydrogenated at 1 atm and 25° C. for 12 hours. The mixture was then filtered and reduced in vacuo to provide 1.93 g (88% yield) of a clear viscous oil of the title compound. Rf=0.25, 9:1 CHCl3:MeOH)

Example 72

Preparation of N-phenylsulfonyl-L-aspartyl-(β-methyl ester)-L-prolyl-L-argininal

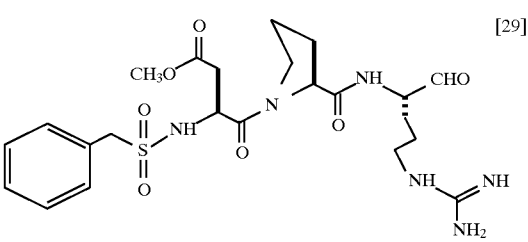

[29]

0.5 g (0.25 mmole protected amino groups) of the resin from Example 7 was placed in a reaction vessel, then was washed three times with 5–10 mL of dichloromethane.

The resin was made ready for use by removing the Boc protecting groups by successive treatment with two 5–10 mL portions of 50% trifluoroacetic acid (in dichloromethane) for a total time of 35 minutes. After neutralizing the acidity by soaking the resin in 5–10 mL of 5% diisopropylethylamine (in dimethylformamide) for 7 minutes, the resin was successively washed two 5–10 mL portions each of dimethylformamide, dichloromethane and dimethylformamide. The deblocked resin was suspended in 5 mL of dimethylformamide, then was treated with NMM (101 mg, 1.0 mmole), N-Boc-L-proline (215 mg, 1.0 mmole), BOP (443 mg, 1.0 mmole), HOBt (135 mg, 0.9 mmole), and DMF (5 mL). After two hours of agitation at room temperature (20°–25° C.), the resin was filtered off and was successively with three 5–10 mL portions of dimethylformamide, dichloromethane.

The resin (coupled to N-Boc-L-proline) was made ready for use by removing the Boc protecting groups (from the coupled Boc-L-proline) by successive treatment with two 5–10 mL portions of 50% trifluoroacetic acid (in dichloromethane) for a total time of 35 minutes. After neutralizing the acidity by soaking the resin in 5–10 mL of 5% diisopropylethylamine (in dimethylformamide) for 7 minutes, the resin was successively washed two 5–10 mL portions each of dimethylformamide, dichloromethane and dimethylformamide. This deblocked resin was suspended in 5 mL of dimethylformamide, then was treated with NMM (101 mg, 1.0 mmole), compound of Example 71 (284 mg, 1.0 mmole), BOP (443 mg, 1.0 mmole), HOBt (135 mg, 0.9 mmole), and DMF (5–10 mL). After two hours of agitation at room temperature (20°–25° C.), the resin was filtered off and was successively treated with three 5–10 mL portions of dimethylformamide, dichloromethane.

The pure title compound was recovered from the resin by by its removal as a semicarbazone, conversion to crude title compound and purification as described in Example 62. Fast atom bombardment mass spectrometry confirmed the theoretical molecular weight of 538 a.m.u.

Example 73

Preparation of N-cyclohexylsulfamyl-L-aspartic acid-(β-methyl ester) -O-benzyl ester

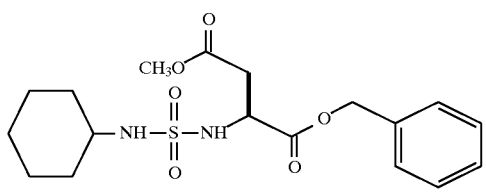

[105]

To cyclohexylamine sulfamic acid sodium salt (Aldrich, 2.01 g, 10.0 mmole) is added 6 mL phosphorousoxychloride. The suspension is then heated to 100° C. for 4 hours. The mixture is then cooled t o room temperature and the phosphorousoxychloride is stripped off in vacuo to provide a solid. This solid is then suspended in dry acetonitrile (35 mL) and the mixture is cooled to 0° C. To this mixture is added the aspartic acid-(β-methyl ester) benzyl ester hydrochloride salt of Example 70 (2.73 g, 10.0 mmole) followed by pyridine (2.6 mL, 30.0 mmole). The mixture is allowed to warm to room temperature in the ice bath over 10 hours. The acetonitrile is stripped off in vacuo and the remaining material is taken up in ethyl acetate. The organic phase is washed with saturated aqueous sodium bicarbonate, brine and 1M aqueous HCl. The organic phase is dried over magnesium sulfate, filtered and reduced in vacuo to provide the title compound.

Example 74

Preparation of N-cyclohexylsulfamyl-L-aspartic acid-(β-methyl ester)

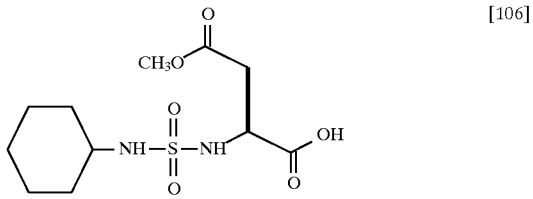

[106]

The compound of Example 73 is dissolved in 100 mL of a 1:1 mixture of tetrahydrofuran/methanol and 0.5 g of 10% Pd/C is added. The mixture is hydrogenated at 1-atmosphere of hydrogen for 4 hours at room temperature. The mixture is then filtered and reduced in vacuo to provide the title compound.

Example 75

Preparation of N-cyclohexylsulfamyl-L-aspartyl-(β-methyl ester)-L-proline-O-benzyl ester

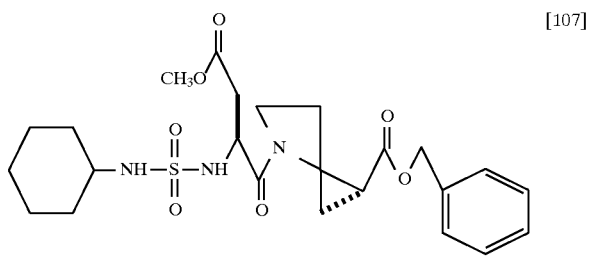

[107]

To a solution of the compound of Example 74 (2.46 g, 8.0 mmole) in dry dimethylformamide (10 mL) is added EDC (8.0 mmole, 1.53 g) and HOBt (10 mmole, 1.62 g) all at once. This mixture is stirred at 0° C. for 10 minutes, then L-proline-(O-benzyl ester) hydrochloride (8 mmole, 1.93 g) is added followed by NMM (24 mmole, 2.6 mL). The reaction is allowed to come to room temperature in an ice bath over 10 hours. The reaction mixture is then diluted with ethyl acetate and is washed with saturated aqueous sodium bicarbonate, brine and 1M aqueous HCl. The organic phase is dried over magnesium sulfate, filtered and reduced in vacuo to provide the title compound.

Example 76

Preparation of N-cyclohexylsulfamyl-L-aspartyl-(β-methyl ester)-L-proline

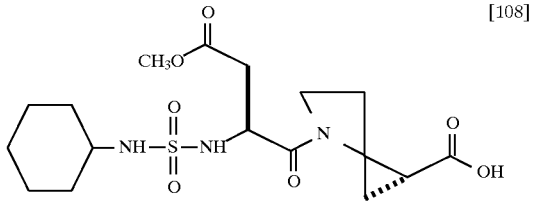

[108]

To a solution of the compound of Example 75 (2.97 g, 6.0 mmole) in methanol (60 mL) is added 10% Pd/C and the mixture is hydrogenated at atmospheric pressure for 12 hours. The mixture is then filtered through a pad of celite and the solvent is removed in vacuo to provide the title compound.

Example 77

Preparation of N-cyclohexylsulfamyl-L-aspartyl-(β-methyl ester)-L-prolyl-L-argininal

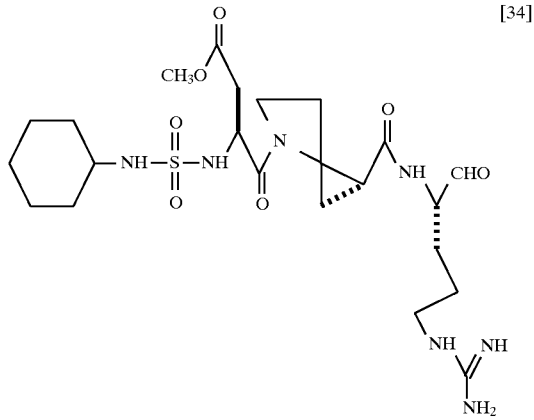

[34]

The title compound is made in the same manner as described in Example 62 substituting the compound of Example 76 (1.0 mmole) for the compound of Example 61.

Example 78

Preparation of N-methoxysulfonyl-L-aspartyl-(β-methyl ester)-L-proline-O-benzyl ester

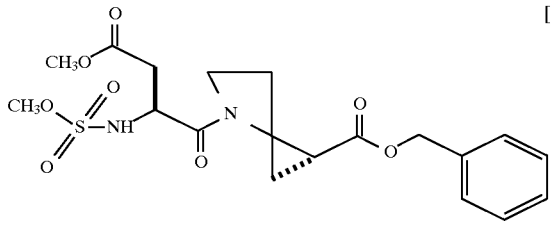

[109]

To methyl sulfate sodium salt (Aldrich, 1.34 g, 10.0 mmole) is added 10 mL phosphorousoxychloride and the mixture heated to 100° C. for 3 hours. The reaction is cooled to room temperature and the phosphorousoxychloride removed in vacuo to leave a white residue. The residue is then mixed with dry acetonitrile (25 mL) and cooled to 0° C. in an ice bath. Then aspartic acid-(β-methyl ester) benzyl ester hydrochloride salt of Example 70 (3.7 g, 10 mmole) is added all at once followed by pyridine (2.6 mL, 30 mmole). The reaction is allowed to warm to room temperature in the ice bath over 10 hours. The acetonitrile is removed in vacuo and the residue diluted with ethyl acetate. The organic phase is washed with saturated aqueous sodium bicarbonate, brine and 1M aqueous HCl. The organic phase is dried over magnesium sulfate, filtered and the solvent removed in vacuo to provide the title compound.

Example 79

Preparation of N-methoxysulfonyl-L-aspartyl-(β-methyl ester)-L-proline

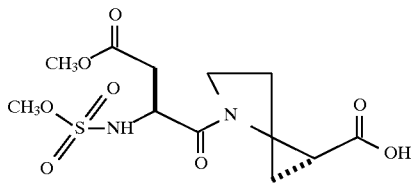

[110]

The compound of Example 78 is dissolved in 150 mL of methanol and 0.5 g of 10% Pd/C is added. The mixture is then hydrogenated at atmospheric pressure for 4 hours. The mixture is filtered and the solvent removed in vacuo to provide the title compound.

Example 80

Preparation of N-methoxysulfonyl-L-aspartyl-(β-methyl ester)-L-prolyl-L-argininal

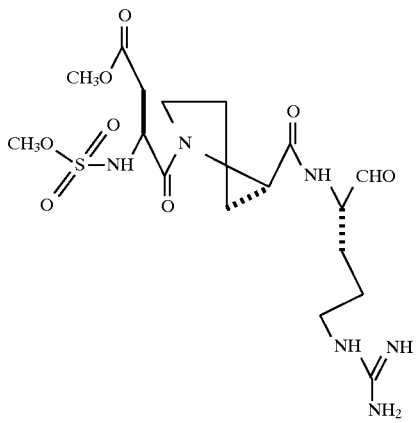

[35]

The title compound is made in the same manner as described in Example 72, substituting the compound of Example 79 (1.0 mmole) for the compound of Example 71.

Example A

In Vitro Inhibition of Selected Purified Coagulation Enzymes

The ability of the compounds of the present invention to act as inhibitors of thrombin, factor Xa and plasmin catalytic activity was assessed by determining the concentration which inhibited enzyme activity by 50%, ($IC_{50}$), using the purified human enzymes.

The buffer used for all assays was HBSA (10 mM HEPES, pH 7.5, 150 mM sodium chloride, 0.1% bovine serum albumin). The assay for $IC_{50}$ determinations was conducted by combining in appropriate wells of a Corning microtiter plate, 50 μL of HBSA, 50 μL of the test compound at a specified concentration (covering a broad concentration range) diluted in HBSA (or HBSA alone for $V_o$ (uninhibited velocity) measurement), and 50 μL of the enzyme diluted in HBSA. Following a 30 minute incubation at ambient temperature, 50 μL of the substrate at the concentrations specified below, was added to the wells yielding a final total volume of 200 μL. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Thrombin Assay

Thrombin catalytic activity was determined using the chromogenic substrate Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 300 μM (about 10-times Km). Purified human (α-thrombin was obtained from Enzyme Research Laboratories, Inc. The enzyme was diluted into HBSA prior to the assay in which the final concentration was 0.25 nM.

Factor Xa Assay

Factor Xa catalytic activity was determined using the substrate, S2765 (N-α-benzyloxycarbonyl-D-argininyl-L-glycyl-L-arginine-p-nitroanilide dihydrochloride) which was obtained from Kabi Diagnostica. The substrate was made up in deionized water followed by dilution in HBSA prior to the assay in which the final concentration was 250 μM (about 5-times Km). Human factor Xa was prepared from purified human factor X obtained from Enzyme Research Laboratories according to the method described by Bock, P. E. et al., Archives of Biochem. Biophys. 273: 375 (1989). The enzyme was diluted into HBSA prior to the assay in which the final concentration was 0.5 nM.

Plasmin Assay

Plasmin catalytic activity was determined using the chromogenic substrate, S-2251 [D-valyl-L-leucyl-L-lysine-p-nitroanilide dihydrochloride], which was obtained from Kabi Diagnostica. The substrate was made up in deionized water followed by dilution in HBSA prior to the assay in which the final concentration was 300 μM (about 5-times Km). Purified human plasmin was obtained from Enzyme Research Laboratories, Inc. The enzyme was diluted into HBSA prior to assay in which the final concentration was 1.0 nM.

Table I below gives the $IC_{50}$ values for selected test compounds compared to the control compound, Boc-(D-Phe)-Pro-Arg-al.

TABLE I $IC_{50}$'s of Selected Compounds Described in the Text.

| Compound | $IC_{50}$ (nM) | | |
|---|---|---|---|
| | Thrombin | FXa | Plasmin |
| 4MeV-Ala(Tzl)-Pro-Arg-al | 88 | 64.5 | 500 |
| 4MeV-Asp-Pro-Arg-al | 139 | 74 | 396 |
| HCA-Asp-Pro-Arg-al (Example 10) | 92 | 52 | 481 |
| HCA-Asp(OCH$_3$)-Pro-Arg-al | 44 | 213 | 546 |
| 2PrPent-Asp-Pro-Arg-al | 6.2 | 241 | 254 |
| 2PrPent-Asp(OCH$_3$)-Pro-Arg-al | 0.80 | 301 | 261 |
| ChxPA-Asp-Pro-Arg-al | 41 | 24 | 250 |
| ChxPA-Ala(Tzl)-Pro-Arg-al | 9.2 | 17 | 48 |
| ChxAc-Asp-Pro-Arg-al | 47 | 15 | 75 |
| BzlSO$_2$-Asp(OCH$_3$)-Pro-Arg-al | 5.0 | 30 | 15 |
| 2-NpSO$_2$-Asp(OCH$_3$)-Pro-Arg-al | 0.62 | 4.3 | 106 |
| n-BuSO$_2$-Asp(OCH$_3$)-Pro-Arg-al | 3.7 | 15 | 250 |
| (4-MePh)SO$_2$-Asp(OCH$_3$)-Pro-Arg-al | 1.1 | 9.5 | 111 |
| Boc-(D-Phe)-Pro-Arg-al | 3.6 | 5300 | 144 |

This data demonstrated the utility of this class of inhibitors as inhibitors of selected enzymes involved in the process of blood coagulation.

Example B

Experimental Model of Thrombosis

The antithrombotic properties of the compound of Example 10, HCA-Asp-Pro-Arg-al, was evaluated using the following established experimental model of acute arterial thrombosis which was a rat model of $FeCl_3$-induced platelet-dependent arterial thrombosis.

This is a well characterized model of platelet dependent, arterial thrombosis which has been used in the evaluation potential antithrombotic compounds such as direct thrombin inhibitors. See, Kurz, K. D., Main, B. W., and Sandusky, G. E., Thromb. Res., 60: 269–280 (1990). Thrombus development in this model is relatively heparin insensitive which suggests that this model may be more representative of the type of thrombosis which has been observed clinically in newly re-canalized coronary vessels following balloon angioplasty or enzymatic thrombolysis. In this model a platelet-rich, occlusive thrombus is formed in a segment of the rat carotid artery treated with a fresh solution of $FeCl_3$ absorbed to a piece of filter paper. The $FeCl_3$ is thought to diffuse into the treated segment of artery and causes de-endothelialization resulting in thrombus formation. The effect of a test compound on the incidence of occlusive thrombus formation following the application of the $FeCl_3$ is monitored by ultrasonic flowtometry and is used as the primary end point. The use of flowtometry is a modification of the original procedure in which thermal detection of clot formation was employed. Kurz, K. D., Main, B. W., and Sandusky, G. E., Thromb. Res., 60: 269–280 (1990).

Male Harlan Sprague Dawley rats (420–450 g) were acclimated at least 72 hours prior to use and fasted for 12 hours prior to surgery with free access to water. The animals were prepared, anesthetized with Nembutal with catheters for blood pressure monitoring, drug and anesthesia delivery implanted. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline infusion) or treatment group with test compound (of Example 10) with at least 6 animals per group per dose. The test compounds were administered after placement of the flow probe and stabilization of the preparation for a period of 30 minutes prior to the thrombogenic stimulus. At t=0, a 3 mm diameter piece of filter paper (Whatman #3) soaked with 10 mL of a 35% solution of fresh $FeCl_3$ (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point. Following the 60 minute observation period the flow probe was removed and the area cleared of all excess fluid. The distal and proximal sutures were tied off and arterial clamps placed on the far proximal and distal ends of the segment. The isolated segment was cut out, blotted dry on filter paper and weighed. The segment was re-weighed following removal of the clot and the difference recorded as total % clot weight. The animals were then euthanized.

The efficacy of the compound of Example 10 as an antithrombotic agent in this in vivo model was demonstrated by the reduction in the incidence of occlusion and in clot size, as shown in Table II below.

TABLE II

Results of the Compound of Example 10 in the FeCl₃ Model of Thrombosis in Rats.

| Treatment Group[a] | Incidence of Occlusion[b] | Clot Size[c] |
|---|---|---|
| Control | 10/10 | 68.65 ± 3.75 |
| Group 1 | 5/6 | 48.38 ± 24.71 |
| Group 2 | 1/5* | 22.38 ± 21.0*** |
| Group 3 | 0/5* | 3.38 ± 5.44*** | a-Control-no treatment
Group 1-25 µg/kg/min i.v. infusion
Group 2-50 µg/kg/min i.v. infusion
Group 3-100 µg/kg/min i.v. infusion
b-Occlusion is defined as the establishment of zero blood flow through the treated segment of the carotid artery.
c-Clot size is defined as: [Isolated clot/(Intact segment-Empty segment)] × 100. Numbers represent the mean ± S.E.M. (n = 6).
*Two-Tailed $P \leq 0.005$ vs Control by Fishers Exact Test.
***$p < 0.01$ vs Control by one-way ANOVA followed by Newman-Kuels Test.

These in vivo data clearly demonstrated the antithrombotic efficacy of the compound of Example 10 in this well established model of experimental thrombosis.

We claim:

1. A compound of the formula

AcR-A₁-L-Pro-Arg-al wherein AcR is a hydrophobic acyl or hydrophobic sulfonyl group; A₁ is an amino acid which has a side chain of the formula —(CH₂)ₘR₂ wherein m is 1 or 2 and R₂ is —CO₂H, —CO₂R' or a tetrazole moiety optionally substituted with R' wherein R' is alkyl of 1 to about 6 carbon atoms, aryl of about 6 to about 14 carbon atoms or aralkyl of about 6 to about 15 carbon atoms, and wherein said compound has an IC₅₀ for thrombin and/or Factor Xa of about 200 nM or less and an IC₅₀ for plasmin which is greater than the smaller of the IC₅₀ for thrombin or for Factor Xa.

2. A compound according to claim 1 wherein A₁ is Glu or Asp.

3. A compound according to claim 1 wherein A₁ is glutamic acid γ-methyl ester or aspartic acid β-methyl ester.

4. A compound according to claim 1 wherein R₂ is a tetrazole moiety.

5. A compound of the formula

AcR-A₁-L-Pro-Arg-al wherein AcR is a hydrophobic acyl or hydrophobic sulfonyl group; A₁ is an amino acid which has a carboxyalkyl side chain or an ester thereof, or is an amino acid having a side chain of the formula —(CH₂)ₘR₂ wherein R₂ is a tetrazole moiety optionally substituted with alkyl of 1 to about 6 carbon atoms, aryl of about 6 to about 14 carbon atoms or aralkyl of about 6 to about 15 carbon atoms and m is 1 or 2, and wherein said compound has an IC₅₀ for thrombin and/or Factor Xa of about 200 nM or less and an IC₅₀ for plasmin which is greater than the small of the IC₅₀ for thrombin and for Factor Xa.

6. A compound according to claim 5 wherein A₁ is Asp or Glu.

7. A compound according to claim 5 wherein A₁ is an amino acid which has a carboxyalkyl side chain esterified with R' wherein R' is alkyl of 1 to about 6 carbon atoms, aryl of about 6 to about 14 carbon atoms or aralkyl of about 6 to about 15 carbon atoms.

8. A compound according to claim 5 wherein A₁ has a carboxyalkyl side chain esterified with an alkanol moiety of 1 to about 6 carbon atoms or a hydroxyaryl moiety of about 6 to about 14 carbon atoms.

9. A compound according to claim 5 wherein A₁ has a carboxyalkyl side chain esterified with a substituent of the formula —O—R' wherein R' is aralkyl of about 6 to about 15 carbon atoms.

10. A compound according to claim 5 wherein R₂ is a tetrazole moiety.

11. A pharmaceutical composition for treating or decreasing the incidence of a condition in a mammal characterized by abnormal thrombosis which comprises a therapeutically acceptable carrier and a compound of any of claims 1 to 10.

12. A method for treating or decreasing the incidence of a condition in a mammal characterized by abnormal thrombosis, which comprises administering to said mammal a therapeutically effective amount of a compound of any of claims 1 to 10.

* * * * *